(12) United States Patent
Buchanan et al.

(10) Patent No.: US 10,071,902 B2
(45) Date of Patent: Sep. 11, 2018

(54) METHOD FOR ASSEMBLING CONDUCTIVE PARTICLES INTO CONDUCTIVE PATHWAYS AND SENSORS THUS FORMED

(75) Inventors: Mark Buchanan, Oslo (NO); Matti Knaapila, Drammen (NO); Geir Helgesen, Finstadjordet (NO); Henrik Hoeyer, Skien (NO)

(73) Assignee: CONDALIGN AS, Kjeller (NO)

( * ) Notice: Subject to any disclaimer, the term of this patent is extended or adjusted under 35 U.S.C. 154(b) by 1051 days.

(21) Appl. No.: 13/992,517

(22) PCT Filed: Dec. 7, 2011

(86) PCT No.: PCT/EP2011/072113
§ 371 (c)(1),
(2), (4) Date: Jun. 7, 2013

(87) PCT Pub. No.: WO2012/076612
PCT Pub. Date: Jun. 14, 2012

(65) Prior Publication Data
US 2013/0320467 A1    Dec. 5, 2013

(30) Foreign Application Priority Data

Dec. 8, 2010  (NO) .................................. 20101714
Oct. 27, 2011  (SE) ...................................  1151005

(51) Int. Cl.
*B81B 3/00* (2006.01)
*G01N 29/02* (2006.01)
(Continued)

(52) U.S. Cl.
CPC .......... *B81B 3/0018* (2013.01); *B81C 1/0015* (2013.01); *G01N 29/022* (2013.01);
(Continued)

(58) Field of Classification Search
None
See application file for complete search history.

(56) References Cited

U.S. PATENT DOCUMENTS

| 4,170,677 A | 10/1979 | Hutcheson |
| 5,313,840 A | 5/1994 | Chen et al. |

(Continued)

FOREIGN PATENT DOCUMENTS

| DE | 10 2007 037 841 A1 | 2/2009 |
| EP | 0 595 532 A1 | 5/1994 |

(Continued)

OTHER PUBLICATIONS

Xu (Carbon 43 (2005) 1479-1487).*

(Continued)

*Primary Examiner* — Joel G Horning
(74) *Attorney, Agent, or Firm* — Oblon, McClelland, Maier & Neustadt, L.L.P.

(57) ABSTRACT

A sensor is achieved by applying a layer of a mixture that contains polymer and conductive particles over a substrate or first surface, when the mixture has a first viscosity that allows the conductive particles to rearrange within the material. An electric field is applied over the layer, so that a number of the conductive particles are assembled into one or more chain-like conductive pathways with the field and thereafter the viscosity of the layer is changed to a second, higher viscosity, in order to mechanically stabilize the material. The conductivity of the pathway is highly sensitive to the deformations and it can therefore act as deformation sensor. The pathways can be transparent and is thus suited for conductive and resistive touch screens. Other sensors such as strain gauge and vapor sensor can also be achieved.

26 Claims, 13 Drawing Sheets

(51) Int. Cl.
*G06F 3/044* (2006.01)
*G06F 3/045* (2006.01)
*B81C 1/00* (2006.01)

(52) U.S. Cl.
CPC .............. *G06F 3/044* (2013.01); *G06F 3/045* (2013.01); *G06F 2203/04103* (2013.01)

(56) References Cited

U.S. PATENT DOCUMENTS

| | | |
|---|---|---|
| 6,194,769 B1 | 2/2001 | Martin et al. |
| 2002/0149466 A1 | 10/2002 | Sunshine et al. |
| 2003/0102154 A1 | 6/2003 | Haba |
| 2007/0138583 A1* | 6/2007 | Ofek ................... B82Y 5/00 257/417 |
| 2009/0038832 A1 | 2/2009 | Chaffins et al. |
| 2009/0305135 A1* | 12/2009 | Shi ..................... B82Y 30/00 429/217 |
| 2012/0224285 A1 | 9/2012 | Svasand et al. |
| 2012/0240992 A1 | 9/2012 | Svasand et al. |

FOREIGN PATENT DOCUMENTS

| | | |
|---|---|---|
| WO | WO 2009/023584 A2 | 2/2009 |
| WO | WO 2010/151141 A1 | 12/2010 |

OTHER PUBLICATIONS

Hernendez (Scripta Materialia 58 (2008) 69-72).*
Martin (Polymer 46 (2005) 877-886).*
Matthias-Klaus Schwarz, et al., "Alternating electric field induced agglomeration of carbon black filled resins", Polymer, 2002, Elsevier Science Ltd., XP004343311, vol. 43, No. 10, pp. 3079-3082.
Chen Wei, et al., "Multifunctional Chemical Vapor Sensors of Aligned Carbon Nanotube and Polymer Composites", J. Am. Chem. Soc. 2006, vol. 128, No. 5, pp. 1412-1413.
Norwegian Search Report dated Jul. 8, 2011 in Patent Application No. 20101714 Filed Dec. 8, 2010 (with English translation of Category of cited document).
Swedish Search Report dated Apr. 19, 2012 in Patent Application No. 1151005-4 Filed Oct. 27, 2011.
International Search Report dated Mar. 23, 2012 in PCT/EP2011/072113 Filed Dec. 7, 2011.

* cited by examiner

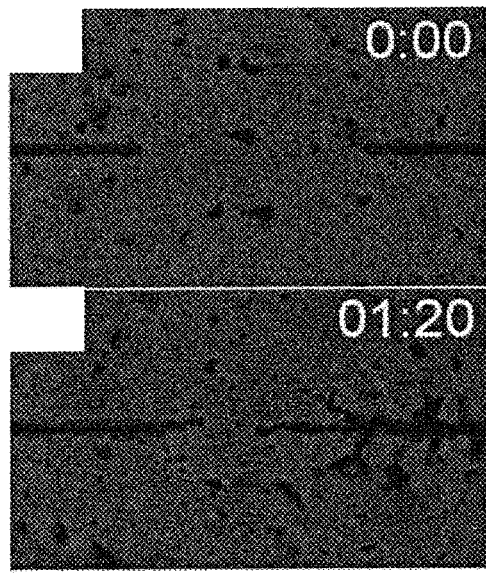
FIG. 13A   FIG. 13B
FIG. 13C   FIG. 13D
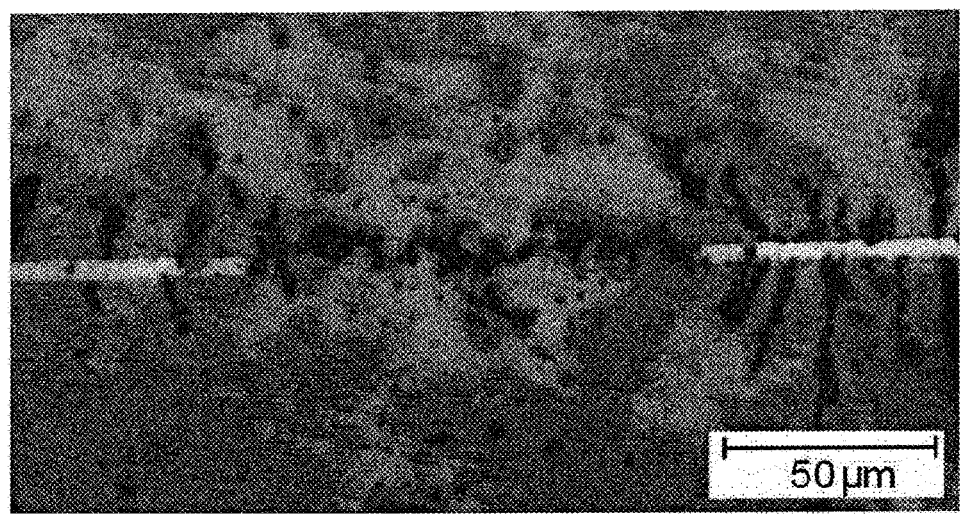
FIG. 14

METHOD FOR ASSEMBLING CONDUCTIVE PARTICLES INTO CONDUCTIVE PATHWAYS AND SENSORS THUS FORMED

TECHNICAL FIELD

The invention concerns a method for forming a well-defined micrometer scale conductive wire or pathway comprising conductive particles on a generic substrate using an electric field. The pathway can be covered by non-conductive organic material like polymer. The pathway connects its ending points electrically, but the strength of this connection can vary with the substrate deformations, the pathway thus acting as a deformation sensor as the conductance and admittance change. The pathway structure is more sensitive to the deformations compared to the randomly oriented mesh. Pathways may also act as a capacitive sensor, and the features can be combined in a hybrid sensor. Such sensors can be used in different areas including nanomechanical cantilever sensors, cantilever sensors and touchscreens.

BACKGROUND OF THE INVENTION

Electrically conductive organic material containing materials can be based on the mixture of polymer-containing matrix and conductive particles (fillers) embedded into this matrix. In the former case the matrix can also contain organic or inorganic additives and the electrically conductive particles either carbon, metal or metal oxide particles. The materials can also be directionally conductive.

In Sensors 2008 8 1595 (Maria Nordstrom & al. published 10 Mar. 2008 ISSN 1424-8220) it is illustrated how the conductivity of organic conductive layer on the substrate can vary with the deformations of the substrate. If the substrate deformations vary as a response to an external input, the conductivity variation can be used to sense this input, and the whole system forms a sensor. Ultimately, the layer can be located on a force microscope cantilever, particularly on an atomic force microscope (AFM) cantilever, whose tip is detecting a sample surface which acts as an external input for cantilever deformation.

In these cases, the conductive organic layer contains conductive particles or polymers that form a random network. When the substrate is bending in one direction, the conductive paths are loosened or broken in this direction but not perpendicular to it. Thus, the conductivity of the organic layer is not anisotropic in the first place, and the particle connections perpendicular to the deformation are essentially not influenced by deformation and are thus not contributing to the sensing phenomenon. There is a need for a sensor where the pathways are directed in this same direction, parallel to the deformation, thus being more sensitive to substrate bending.

A touch screen is an electronic visual display that can detect the presence and location of a touch within the display area using e.g. a finger, a hand or a stylus. Touch screens are used in many digital appliances, such as mobile phones, personal computers, electronic books, satellite navigation devices and video games.

A resistive touch screen panel is usually composed of layers using two thin, electrically conductive layers separated by a narrow gap. When an object, such as a finger, presses down on a point on the panel's outer surface, the two layers become connected at that point: the panel then behaves as a pair of voltage dividers with connected outputs. This causes a change in the electrical current, which is registered as a touch event and sent to a controller for processing. A resistive touch screen can also be piezoresistive; when pressed the conductivity of the material or wires increase and the controller detects where.

A capacitive touch screen panel consists of an insulator such as glass, coated with a transparent conductor such as indium tin oxide. As the human body is a conductor, touching the surface of the screen results in a distortion of the screen's electrostatic field, measurable as a change in capacitance. Different technologies known to someone skilled in the art may be used to determine the location of the touch. The location is then sent to a controller for processing. Examples of controllers are 3M Touch EX II 7000 Series for a capacitive screen or Semtech SX8650 for a resistive screen.

A touch screen can also combine capacitive and resistive sensing, e.g. detecting the proximity of one or more fingers, resulting in one action, and detecting one or more fingers tapping the screen resulting in another action. US20090189875A1 teaches one method for constructing a hybrid touch screen.

Problems with the current technologies for producing touchscreen panels are that transparent conductors such as indium tin oxide are expensive and have limited durability, and that resistive screens must be produced with several layers.

Nanomechanical cantilevers can be produced as micro fabricated silicon beams or using piezoelectric materials, as taught in U.S. Pat. No. 7,458,265. They are used as mechanical sensors, useful as mass and viscosity sensors, which transform processes occurring at their surface into a mechanical response. This signal transduction principle allows surface stress measuring at the cantilever surface by monitoring the bending of the cantilever and at the same time observing changes in the oscillation properties of the cantilever related to changes in mass load on the cantilever. Nanomechanical cantilevers can be used for chemical sensing such as detection of heavy metals, and as biosensors, e.g., for DNA and protein detection. Arrays of cantilever sensors can be employed for the parallel detection of multiple molecules of interest. Also, nanomechanical cantilever sensors can be used in surface and materials sciences for the real-time monitoring of self-assembled monolayer (SAM) formation, the detection of cholesterol interaction with hydrophobic surface layers and to study layer-by-layer build-up processes in real-time are possible, refer to Journal of Nanoscience and Nanotechnology, Volume 10, Number 4, April 2010 Koeser, Joachim & al: Nanomechanical Cantilever Sensors as a Novel Tool for Real-Time Monitoring and Characterization of Surface Layer Formation.

Touch sensors can be made by using Quantum Tunneling Composites (QTC) manufactured by Peratech Ltd. QTC is made from conductive filler particles, e.g. metal particles, combined with an elastomeric binder, typically silicone rubber, disclosed in WO/1999/038173. The metal particles are given an irregular structure with a spiked surface which is electrically insulated by the silicone rubber. The rubber allows the particles to get close but not touch even when the material is pressed or densely loaded. Increased charge on the spikes decrease the effective width of the potential barrier in quantum tunneling. This reduces the distance and energy required for the electron charge to tunnel through, and the material becomes conductive. The system with spiky particles is far more sensitive than the system with rounded particles would be. The conductance varies with the dynamic conditions. QTC are in general isotropic. There is a need for making anisotropic QTC in order to manufacture improved sensors.

"Multifunctional Chemical Vapor Sensors of Aligned Carbon Nanotube and Polymer Composites" by Wei & al. J. Am. Chem. Soc., 2006, 128 (5), pp 1412-1413, DOI: 10.1021/ja0570335 describes how partially coated perpendicularly aligned carbon nanotube arrays with an appropriate polymer thin film along their tube length can be used as sensors for chemical vapours, and also for mechanical deformations, thermal and optical exposures.

U.S. Pat. No. 7,777,478 discloses sensors based on nanotubes that can be used as touch and auditory sensors. In a similar way, US7673521 teaches how carbon nanotubes are grown from organometallic and incorporated into a polymer matrix to form a nanosensor which provides information regarding a physical condition of a material such as an airplane chassis or wing, in contact with the nanosensor.

There is a need for a better way to grow aligned conductive paths in a matrix, to form such sensors.

The object of the invention is to fulfil one or more or the above-mentioned needs, or to provide a useful alternative to existing methods and products.

DESCRIPTION OF THE INVENTION

The invention provides for a method for forming a sensor on a substrate in accordance with claim 1. In accordance with the method, one or more conductive wires or pathways of conductive particles are formed.

The conductive pathway can be embedded in a matrix. The matrix could be organic, like a polymer, or inorganic, like inorganic polymer or glass. The pathways are formed located on a substrate covered with matrix, in a matrix that is or becomes a part of the substrate, or placed on a substrate after being formed in a matrix.

The term "substrate" is in this disclosure used for all these embodiments, and the term "matrix" may include the substrate.

The terms "wire" and "pathway" and "string" are used interchangeably. Moreover, the terms "single wire" or "a stringlike formation" are used interchangeably.

The term "conductivity" is used for both electric conductance and electric admittance. The inventions can thus be used for both sensing changes in direct (DC) or alternate current (AC).

The term "sensor" is used both for the pathway itself, as its electromagnetic properties are changed, as disclosed below, and for the complete arrangement that includes the controllers and auxiliary circuits that is needed to form a sensor that can be applied e.g. as a touch sensor or a cantilever sensor.

The conductivity of the pathways is varied with deformation of the substrate. The substrate can be deformed by pressing. The substrate can also be deformed from bending or pulling or by other forces, such as gravity or electromagnetic forces. The conductivity change is in the alignment direction of the one or more pathways, which makes the pathways act as a deformation sensor.

The pathways can also be used as a capacitive sensor using capacitive coupling between the pathway and an object or human. Capacitive sensors detect anything which is conductive or having dielectric properties. Multi-touch and gesture-based touchscreens are premised on capacitive sensing and can be made using the present invention.

A combined resistive and capacitive sensor can also be produced, useful for touchscreens.

Conductive particles in a matrix can be assembled by an electric field into aligned pathways. After the alignment step the matrix and thus conductive pathways is stabilized for example by curing (thermoset matrix), by lowering the temperature (thermoplastic or thermotropic matrix or glass) or by evaporating the accompanying solvent off (lyotropic matrix). The pathways can remain embedded in the substrate or be exposed on its surface, if parts of the matrix is removed or cleaved, e.g. by etching or burning or pyrolysis.

The method comprises the steps of first applying a layer of a matrix and conductive particles over a substrate, when the viscosity of the matrix is low enough to allow the conductive particles to rearrange within the matrix. In a subsequent step an electric field is applied over the matrix, resulting in a number of the conductive particles aligning with the field and thus forming conductive pathways. Thereafter the viscosity of the matrix is changed to a second, higher viscosity, in order to mechanically stabilise the pathways.

Preferably, the conductive particles are formed by infusible particles such as carbon particles or metal oxide or metal particles that have dielectric properties such that they are aligned by a field. Advantageously, the conductive particles show low molecular or particle anisotropy, and thus the major part of the conductive particles has a low aspect ratio; aspect ratio ranges of 1-4, or 1-5, 1-10 or 1-20 are typical. The terms "low molecular or particle anisotropy" and "low aspect ratio" has the same meaning herein. This is the case for example with irregular graphitic particles, spherical carbon black (CB) or disk-like or conical carbon particles here referred to as carbon nanocones (CNC).

The conductive particles can be a mixture of different carbon particles. Also other conductive particles can be used, like metal, such as silver or metal oxide particles or colloidal metal particles. Dielectric particles that are piezoelectric, like lead zirconate titanate (PZT), barium titanate, strontium titanate, lead magnesium niobate, lead titanate solid solutions, strontium lead titanate and lanthanum gallium silicate could be used for giving the pathways piezoelectric features.

The matrix can be a thermoset polymer, which means that it is stabilized by curing which forms permanent chemical cross-links. It can be a thermoplastic polymer system which means that its viscosity is lower at higher temperatures, which allows alignment of particles, and higher at lower temperatures, which allows stabilization of the matrix after alignment. The matrix can be a lyotropic system which means that the matrix can be plasticised by solvent and solidified by evaporating this solvent off.

It can also be any combination of these systems. For example, the lyotropic matrix can contain thermoset polymer that can contain solvent for plasticizing it, but the stabilization can be based both on cross-linking the polymer and also on the solvent evaporation.

The matrix can also comprise a UV-curable polymer, in which case the viscosity may be altered by submitting the matrix to light in the Ultra Violet range. UV-curing is sometimes referred to as photoinitiated polymerization. A UV-curable matrix material may be combined with any of the above-mentioned types of matrix materials to form various alternative matrix materials.

Moreover, the matrix may comprise an elastomer. This provides for possibilities of creating a compressible matrix where the resistance through the conductive path may be decreasing with the compression of the matrix.

The electric field can be created between electrodes that are placed in direct contact with one or both sides of the substrate and matrix, constituting a first layer. The electrodes can also be placed outside additional insulating layers, where the insulating layers are placed in contact with the first layer. The purpose of the insulating layers can be to build capacitive sensors or to build structures where the pathways are partially exposed to other conductive wires or layers and partially insulated from them. The electrodes can also be remote, not in direct contact with the layers.

The direction of the electric field is determined by the electrode arrangement, and thereby the direction of the conductive pathways formed by the aligned conductive particles can be controlled. The pathways can be formed in any direction in the matrix. Pathways can also be formed by moving the electrodes, thus forming pathways that can act as coils or antennas. The pathways can be controlled in three dimensions within the matrix by moving the electrodes and changing the field, or multiple layers can be used.

The electric field can be in the order of 0.05 to 35 kV/cm, or more specifically 0.1 to 10 kV/cm. This means that for a typical alignment distance in the range of 10 µm to 1 mm, the voltage applied can be in the range of 0.1 to 100 V. The field may be an alternating (AC) field, but can also be a direct (DC) electric field. A typical field is an AC field having a frequency of 10 Hz to 10 MHz. Very low frequencies <10 Hz or DC fields lead to asymmetric chain formation and build up. The low voltage needed for applying the method is simple to handle in a production line and does not need the specific arrangements necessary when handling high voltages.

Thus, the present invention is based on the finding that it possible to align conductive particles in fluid-like matrices using an electric field to form conductive pathway in the fluid-like polymer matrices. The pathway is able to enhance the macroscopic conductivity of the material. In particular, the formation of conductive pathways allows the material to become conductive also when it contains a lower amount of conductive particles than what is otherwise necessary for creating electrical contact for the material having randomly distributed particles.

This procedure renders an anisotropic material and a directional conductivity that is higher along the alignment direction than perpendicular to it.

The method can be used to produce a variety of sensors. Possible applications of sensors according to the present invention include but are not limited to:

Touch screens
Cantilever sensor for nanomechanical detection
Structures in microelectromechanical systems (MEMS).
Cantilever arrays as biosensors for medical diagnostic applications
Cantilevers as radio frequency filters and resonators
Cantilever transducers for atomic force microscopy
Moisture detectors
Strain gauges
Nonintrusive bio monitoring A sensor can be formed by connecting a pathway connecting to two or several electrodes on the substrate thus providing an electrical connection between the electrodes. When the substrate is deformed by an external input in the alignment direction of the pathway, this increases distance between the particles at one or more points of the pathway and the conductivity is sharply decreased. Thus, it is possible to measure substrate deformation, such as bending, and thus the external input causing the bending. Depending on the geometry of the pathway and how the deformation is applied, there could also be a decrease of the distance between the particles and conductivity could increase, so that the pathways are not conductive until the matrix is deformed. All these changes are detected by the controller and analysed by the controller or a connected processor, embedded system or computer.

In the case of the pathways being used as a capacitive sensor, it is the capacitance, i.e. the charge held by the pathways, which is changed by conductive coupling from another object or a human. This change is then detected by connected controllers such as 3M Touch EX II 7000 Series, Freescale Semiconductor MPR121 Proximity Capacitive Touch Sensor. The controller is generally a microcontroller-based integrated circuit placed between the sensor (the conductive pathways with the substrate and the circuits that connect them) and a processor such as an embedded system controller or a computer. The controller reads electric information from the sensor and translates it into information suited for the PC or embedded system controller. This information can e.g. be the coordinates for where a finger or object is near or touches the sensor, the strength of the touch, or the number of touches and how the touch moves, as needed for multi-touch applications.

For resistive sensor applications the controller is similar, but it detects changes in conductivity. Some controllers can be strapped to act as either a resistive or capacitive controller, e.g. the 3M Excalibur and ExII chipset. These or other controllers can be used to make a hybrid resistive and capacitive sensor, e.g. for use as a touch screen.

Cantilevered beams are commonly used in the field of microelectromechanical systems (MEMS). MEMS cantilevers can be fabricated from polymers. They can include conductive pathways of the present invention. The fabrication process involves undercutting the cantilever structure to release it, for example with a wet or dry etching technique. When the cantilever vibrates, the vibrations changes the conductivity and capacitance of the pathway, and this can be detected by a controller.

Humidity sensors are generally manufactured using capacitors and resistors. If the matrix consists of a polymer material that is permeable to vapour, e.g water vapour or vapours of alcohols, e.g. using a biopolymer such as cellulose, the conductance and capacitance of the conductive pathways will change when a voltage is applied, and this can be detected by a controller.

A strain is a normalized measure of deformation representing the displacement between particles in the body relative to a reference length. A strain is in general a tensor quantity. A strain gauge is a device used to measure the strain of an object. It can be made using the present invention where the conductive pathways change their conductivity as the object to which the substrate is fastened changes in size and deforms the substrate of the strain gauge. The change of conductivity can be measured using a Wheatstone bridge. The pathways can be straight or have a pattern.

Sensors of the present invention can be used for nonintrusive bio monitoring. For example a pulse can be measured as strain on the skin. Heartbeat and blood flow will result in change of capacitance that can be measured with the present invention configured as a capacitive sensor.

In a particular embodiment, it is suggested to form a conductive pathway comprising CB (carbon black) particles, most preferred assembled into a single wire, in a polymer matrix. Preferably, the polymer may be an UV curable thermoset polymer, and advantageously with a glass transition point below room temperature.

Advantageously, a micro-mechanical strain sensor may be produced made of CB particles, most preferred assembled into a single wire, in a polymer matrix.

Aligned single strings of CB in polymer as well as polymer composites containing CB strings can mimic the piezoresistive properties of carbon nanotubes (CNTs) and the polymer composites containing CNTs, but CB particles provide additional benefits including significantly easier mixing and lower production costs.

Aligned strings make an initially insulating composite conductive and the stretching of strings result in a piezoresistive effect due to the induced displacement of the articles. The strings show gauge factors of about 150 while corresponding films containing 12 vol. % of CB are almost completely insensitive to identical stretching. A gauge factor of 150 significantly exceeds the values of 15-20 previously shown in the prior art for isotropic CB in SU8 polymer (see L. Gammelgaard et al. Appl. Phys. Lett. 88 (2006), 113508).

It is believed that the gauge factor may be varied by varying the particle sizes, particles size distribution and/or by improving the conductivity of the particles.

Advantageously, there may be provided a conductive pathway comprising CB particles in a matrix comprising an elastomer.

In another embodiment, it is proposed to form a conductive pathway comprising carbon nanocones and discs (CNCs), being aligned into a stringlike formation, preferably using an alternative electric field (dielectrophoresis).

Carbon nanocones and discs (CNCs) have intriguing properties including an unique conical topology. CNCs are formed by stacked graphene cells with a tip of 1-5 carbon pentagons, which allow only discrete apex angles for the cone opening: 112.9°, 83.6°, 60.0°, 38.9° and 19.2°.

Advantageously, the CNC particles may initially be dispersed into a polymer matrix with a particle fraction below the percolation threshold of the CNCs. In a particular embodiment, the percolation threshold is about 2 vol. %, and it is suggested to use CNC particles dispersed to less than about 1 vol %, less than about 0.1 vol. % or even less than 0.01 vol %.

A value well below the percolation threshold will suppress particle aggregation and facilitate transparency of the matrix, which is advantageous as it allows the use of an UV-curable polymer for the matrix.

Advantageously, the alignment may be performed using a AC or DC electric field, most preferred an AC field. The voltage may preferably be as mentioned above, 0.05-35 kV/cm, more preferred 0.1 to 10 kV/cm. For an alternating field the frequency may advantageously be as mentioned above: 10 Hz to 10 MHz; In a preferred embodiment using CNC particles 1 kHz and 4 kV/cm was used. The alignment of the particles may develop in minutes and makes the initially insulating, nonaligned material conductive.

The following curing, preferably UV-curing of the polymer matrix, renders a solid state device.

The stretching of the aligned strings in the cured polymer leads to a reversible piezoresistive effect, and a gauge factor of about 50 has been demonstrated. This is in sharp contrast to prior art CNC films with a particle fraction above the percolation threshold (13 vol. %), which are conductive but not sensitive to stretching.

The resulting CNC strings are Ohmic in nature and may show higher DC conductivity (example 22-500 S/M) than identically prepared strings out of carbon black particles (CB) (example 1-22 S/m) (see examples below).

In particular it is suggested to form a micro-mechanical strain sensor based on carbon nanocones and discs (CNCs) which are aligned into stringlike formation as described above.

In addition, it may be mentioned that the methods and sensors described in the above are believed to be suitable for different purposes, including strain, stress or force sensors, for example such as described in WO 2011/079390. In particular, the method may comprise the formation of three dimensional networks of pathways, resulting in sensors comprising such three-dimensional pathways. This type of structures may be particularly advantageous for use in robot skin or machine or device surface applications.

Printing techniques can be used to manufacture layered objects, including mechanical and electronic systems. Thus, using embodiments of the present invention, it is possible to create aligned strings in such a printed layer matrix, or to modify printed strings, e.g. by healing a poorly printed string, or by adding particles of different material, where some could be printed, and some could be in the printed matrix. U.S. Pat. No. 7,766,641B2 "Three dimensional (3D) printer system with placement and curing mechanisms" discloses one example of a printer system with a curing mechanism, that could be used for this purpose.

Moreover, the methods and sensors described herein are believed to be suitable in shear sensors, such as for example those described in U.S. Pat. No. 5,313,840. Here a tactile sensor capable of detecting shear force comprises an anisotropically conductive material disposed between a conductive cursor and an array of contacts. In one embodiment, the anisotropic material is affixed to the contact array, and the cursor is affixed to an elastomeric skin overlying the material. Movement of the cursor is detected b interconnection of the contacts underlying the cursor. In another embodiment, the anisotropic material is affixed to the cursor but is free to move over the contact array in response to shear force.

Movement of the cursor is detected by interconnection of the underlying contacts. Such arrangements can also detect pressure and temperature.

In addition, sensors in accordance with the sensors described herein could be used in several other applications, such as for example:
  Sensors integrated in rubber shoe soles or gloves for monitoring stress,
  Sensors integrated in clothing for monitoring touch, movement or tear.
  Sensors integrated in tires such as car/aircraft tires, using homogenous stress monitoring and/or detection of weakness and of wear and tear,
  Stress and shear sensors for large structures such as buildings, ships, aircrafts or cars.
  Shear measurement sensors used for patients in healthcare
  Sensors for wall shear stress and other shear stress measurements related to engines and machines, e.g. along the combustor wall of an aircraft.

Hence, in a first aspect of the invention, there is provided method for forming a sensor on a substrate, using electrodes forming one or more anisotropic conductive pathways in one or more layers, from mixture comprising matrix and conductive particles comprising the steps
  a) forming a layer of the mixture, the mixture having a first viscosity which allows the conductive particles to rearrange within the layer;
  b) applying an electric field over the layer, so that a number of the conductive particles are assembled and aligned with the field, thus creating one or more conductive pathways;
  c) changing the viscosity of the layer to a second viscosity, said second viscosity being higher than the first viscosity, in order to mechanically stabilise the layer and preserve the one or more conductive pathways.

In certain embodiments, the matrix may be totally or partly removed from the layer after step c.

Advantageously, the conductivity of the pathways is changed if the matrix is deformed.

Preferably, the particles comprise material selected from the group carbon, metal, metal oxides, ceramics, piezoelectric material.

Advantageously, the particles are conductive from quantum tunneling effects.

Preferably, the number of particles in step a) is below a percolation threshold. It is particular advantage of the method proposed herein that the concentration of conductive particles may be low. For conductive mixtures, a percolation threshold is defined as the lowest concentration of conductive particles necessary to achieve long-range conductivity in a random system. The percolation threshold may thus be determined experimentally for a particular combination of matrix and conductive particles.

In a system formed by a method as proposed herein, the concentration of conductive particles necessary for achieving conductivity in a predefined direction may be lower than the percolation threshold, while still providing the necessary conductivity.

For practical reasons, the concentration of particles is determined by the requirements on the conductive pathways. There is usually no reason to have excess amounts of conductive particles not arranged into the conductive pathways. The concentration of conductive particles in the matrix could be up to 10 times lower than the percolation threshold. Concentrations of conductive particles may for example be in the range of 0.2-10 vol %, or 0.2-2 vol % or 0.2-1.5 vol %.

The electric field may advantageously be generated between one or more pairs of alignment electrodes that are at fixed position or that are moved relatively to the substrate.

At least one of the alignment electrodes may be in direct contact with the layer.

Alternatively, the alignment electrodes may be insulated from the layer.

The method may comprise the step of applying either AC or DC-electric field in the order of 0.05-35 kV/cm, and especially in the order of 0.1-10 kV/cm.

Advantageously, the particles have an aspect ratio range of 1-20, more preferred 1-10, more preferred 1-5, most preferred 1-4.

Advantageously, the particles comprise irregular graphitic particles, spherical carbon black (CB) particles or disc-like or conical carbon particles (carbon nanocones CNCs).

Preferably, the matrix is a thermoset polymer, a thermoplastic polymer system, a lyotropic system or a mixture thereof.

Alternatively or in addition thereto, the matrix may comprise a UV-curable polymer.

Alternatively or in addition thereto, the matrix may comprise comprises an elastomer.

The above-mentioned features of a method may be combined to form various embodiments of the invention.

In another aspect of the invention there is provided a sensor being manufacturable by the method in accordance with the above.

In another aspect of the invention, there is provided a sensor manufactured by the method in accordance with the above.

In another aspect of the invention, there is provided a sensor with one or more conductive pathways formed from conductive particles in a matrix wherein the number of particles in the pathways is below the number of particles that constitutes a percolation threshold if the particles were homogenously distributed in the matrix.

Advantageously, the sensor comprises a substrate, and the conductivity of the aligned particles is influenced by the substrate deformations or bending.

Advantageously, the capacitance of the pathways may be influenced by the presence of an object or a human.

Preferably, the particles have an aspect ratio range of 1-20, more preferred 1-10, more preferred 1-5, most preferred 1-4.

Advantageously, the particles comprise irregular graphitic particles, spherical carbon black (CB) particles, or disc-like or conical carbon particles (carbon nanocones CNCs).

The matrix may advantageously be a thermoset polymer, a thermoplastic polymer system, a lyotropic system or a mixture thereof.

Alternatively or in addition thereto, the matrix may comprise a UV-curable polymer.

Alternatively or in addition thereto, the matrix may comprise an elastomer.

Advantageously, the particles may comprise CB particles, preferably being assembled to form a single pathway.

Advantageously, the particles may comprise carbon nanocones and discs (CNCs), preferably being assembled to form a single pathway.

Advantageously, the matrix may comprise a polymer material, preferably a UV-curable polymer material, and most preferred it may also have a glass transition point below room temperature.

Preferably, the sensor may be a micro-mechanical strain sensor.

Advantageously, the substrate may be an AFM cantilever.

The features of a sensor as described above may be combined with each other to form advantageous embodiments.

In another aspect of the invention there is provided the use of a sensor in accordance with the above in a resistive, capacitive or hybrid touchscreen.

In another aspect of the invention there is provided the use of a sensor in accordance with the above in a cantilever sensor In another aspect of the invention there is provided the use of a sensor in accordance with the above in a nanomechanical cantilever sensor In another aspect of the invention there is provided the use of a sensor in accordance with the above as a vapour sensor.

In another aspect of the invention there is provided the use of a sensor in accordance with the above, where the sensor also functions as at least one of an anti-static coating, a thermal conductor, an antenna and an electro-magnetic shielding.

In another aspect of the invention there is provided the use of a sensor in accordance with the above in a robot skin application.

The invention will now be further described with reference to exemplary embodiments and to the drawings, which refer to non-limiting examples only, and wherein:

LIST OF DRAWINGS

FIG. 5 shows schematics of a hybrid touch screen with controllers connected to a processor of a PC, mobile phone or the similar.

FIG. 13A is a micrograph of the assembly of a string of CNCs before the electrical field was applied.

FIG. 13B is a micrograph of the assembly of a string of CNCs at 45 seconds after 45 seconds.

FIG. 13C is a micrograph of the assembly of a string of CNCs after 1 minute and 20 seconds.

FIG. 13D is a micrograph of the assembly of a string of CNCs after 2 minutes and 20 seconds.

FIG. 14 illustrates a string of CNC particles in an embodiment of the invention.

DETAILED DESCRIPTION OF THE INVENTION

Figure 1:
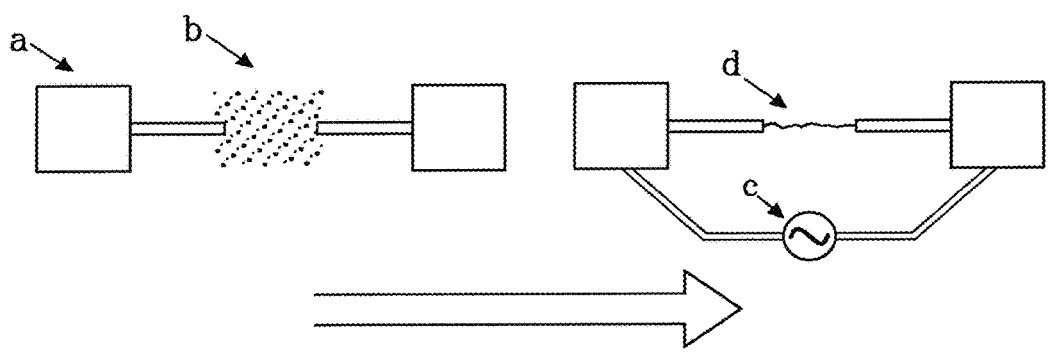
FIG. 1 shows the method of forming aligned particle wires in between two electrodes. The arrow in the Figure indicates the direction of the process.
Figure 2A:
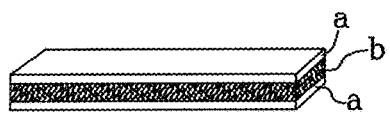
FIG. 2A shows alignment with electrical contacts between electrodes.
Figure 2B:
FIG. 2B shows alignment with electrical contacts between electrodes.
Figure 2C:
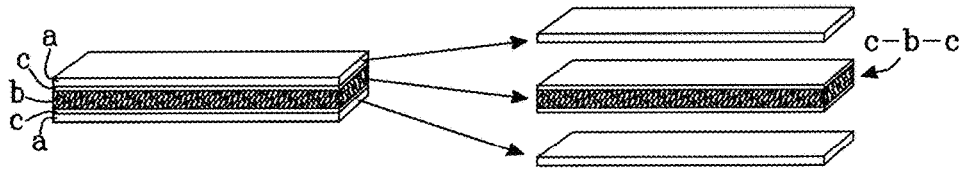
FIG. 2C shows alignment without electrical contacts between electrodes.
Figure 2D:
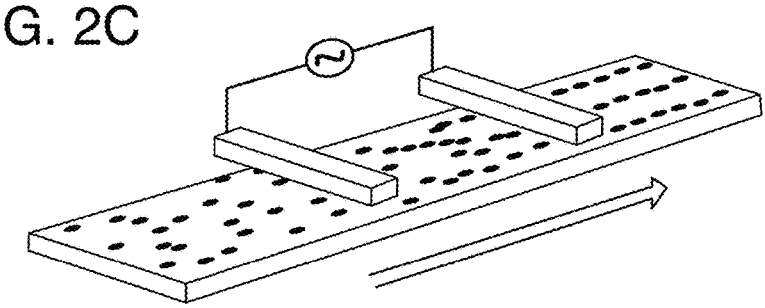
FIG. 2D shows alignment without electrical contacts between electrodes.

In all embodiments, the method comprises the mixing of infusible conductive particles and fluid matrix. The matrix contains at least polymer and potentially solvent. The electric field aligns the conductive particles mixed in this fluid. Control of the viscosity of this mixture is by curing the polymer matrix, e.g. by lowering its temperature or by evaporating solvent off.

The resultant aligned material retains anisotropic properties and has directional electrical conductivity. In this way, aligned conductive microstructures are formed of originally infusible particles.

When the substrate of the aligned pathway is deformed, the conductivity changes. When a conductive or dielectric body is close to the pathway, the capacitance changes.

The sensor is manufactured by performing the steps of
a. forming a layer of the mixture, the mixture having a first viscosity which allows the conductive particles to rearrange within the layer;
b. applying an electric field over the layer, so that a number of the conductive particles are assembled and aligned with the field, thus creating one or more conductive pathways;
c. changing the viscosity of the layer to a second viscosity, said second viscosity being higher than the first viscosity in order to mechanically stabilise the layer and preserve the one or more conductive pathways.

The matrix may be totally or partly removed from the layer after step c. The steps may be repeated to create several layers. The conductive pathways in one layer can be connected to the pathways in other layers. The field in step b) can be changed and moved.

In another embodiment the matrix is partly removed by using a solvent or heat. The conductive pathways are exposed. The matrix is replaced with a polymer having mechanical properties more preferable for its use as a sensor.

The resulting sensor device with one or more conductive pathways formed from conductive particles in a matrix can have a number of particles in the pathways being below the number of particles that constitutes a percolation threshold if the particles were homogenously distributed in the matrix.

The invention will be further described by the following examples. These are intended to embody the invention but not to limit its scope.

Example 1

This example concerns the applicability of the alignment method, the use of alignment for formation of individual aligned chains in the predetermined positions.

The employed conductive particles were carbon black (CB) from Alfa Aesar, carbon nano cones CNC from n-Tec AS (Norway) and iron oxide (FeO.Fe2O3) from Sigma-Aldrich.

The employed polymer matrix was a two component low viscosity adhesive formed by combining Araldite AY 105-1 (Huntsman Advanced Materials GmbH) with low viscosity epoxy resin with Ren HY 5160 (Vantico AG).

The conductive particles were mixed in the adhesive by stirring for 30 minutes. Due to the high viscosity of mixture, efficient mixing is possible only up to 20 vol-%. of particles.

Estimated percolation threshold of these materials are at ~2 vol-%. The mixtures are conductive above and insulators below this threshold. Particle loads of 1/10 of the estimated percolation threshold were used.

The particles in the matrix were aligned using an AC source. In this example the alignment procedure 1 kHz AC-field (0.6-4 kV/cm, rms value) was employed for >10 minutes for >1 mm electrode spacing and <10 minutes for <1 mm electrode spacing.

The curing was performed immediately afterwards at 373 K for 6 minutes.

The electrode area is kept sufficiently small to allow only a single pathway of particles. Alternatively, the particle fraction is lowered. This is shown in FIG. 1.

In one embodiment of this example, metal particles, silver flakes (Sigma-Aldrich) of size 10 μm, was used instead of carbon particles.

Example 2

In FIG. 1b is shown removal of electrodes after alignment and thus freestanding aligned film even in the case where the matrix is adhesive. The alignment also occurs if the electrodes do not touch the material and so the alignment can be performed from the distance. When the material and electrodes are moved, continuous or stepwise, with respect to each other during the alignment, this allows continuous alignment processing and different geometries. Three possible options for the alignment settings are illustrated in FIG. 1b that shows aligned film with (A-B) and without (C-D) electrical contacts between electrodes (a) and material (b). In the case (A) the aligned film forms permanent connection between the electrodes. In the case (B) the electrodes and material are only loosely joined together and can be moved apart after alignment. In the case (C) there are insulating layers (c) between the material and electrodes and they are easily moved apart after the alignment even in the case where the material is an adhesive. In this case the obtained material is a multilayer consisting of aligned layer (b) and two insulating layers (c) In the case (D) the alignment is carried out from the distance and the mutual location of electrodes and film can be additionally moved during the alignment. For illustrative purposes the placement of the electrodes are shown such that alignment occurs in the z-direction. Alignment in the x- and y-direction or an arbitrary direction can be achieved by relative movement of the field, such as moving the distant electrodes.

FIG. 2 shows a picture of a single pathway consisting of an aligned row of particles.

Example 3

This example concerns the applicability of the alignment method, the use of alignment for formation of individual aligned chains in the predetermined positions.

Figure 3:
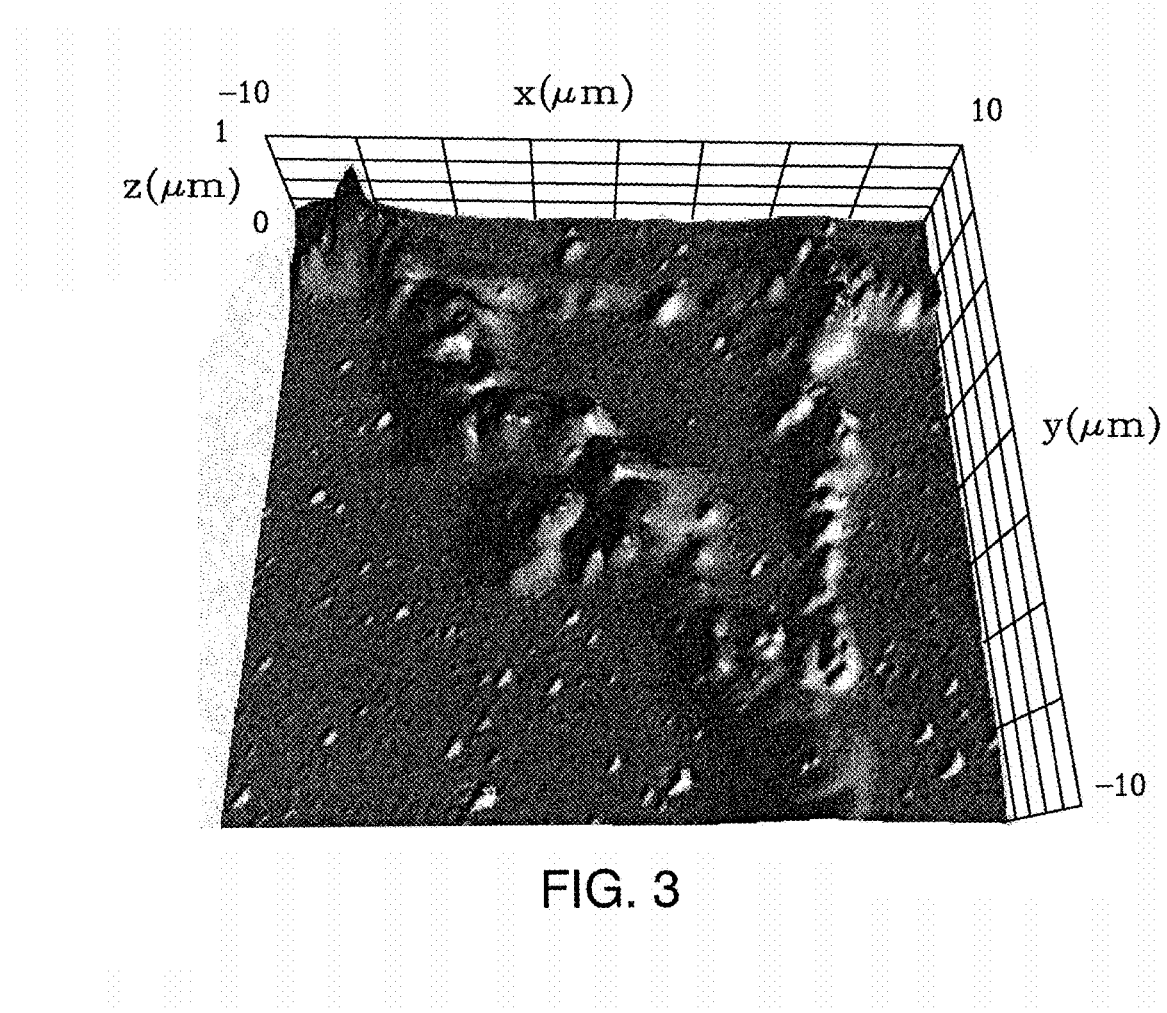
FIG. 3 shows an AFM image of a single aligned particle wire on the generic surface.
Figure 4:
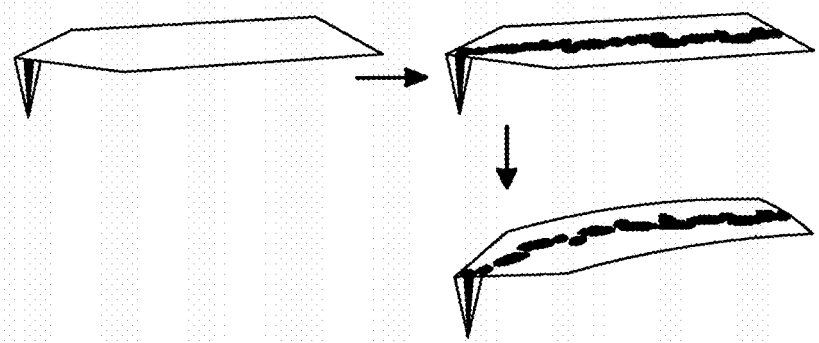
FIG. 4 shows schematics of a single wire on an AFM cantilever.

The procedure was otherwise similar to that in Example 1 but instead of generic surface the particle chain is aligned on the AFM cantilever. When the cantilever is bending, influenced due to the changing surface forces, the aligned pathway gets microscopically stretched and the particles become disconnected from each other. This influences the conductivity through the particle chain. This allows the use of aligned chain as a sensor of surface properties of the surface studied by the cantilever. This setting is illustrated in FIG. 3, where the upper image to the right illustrates a connected path, and the lower image (bent state) illustrates a disconnected path.

Example 4

A resistive touchscreen placed in front of the display is created from two layers of film with conductive pathways in x and y direction, and with the matrix reduced so that the pathways are exposed. When contact is made to the surface of the touchscreen, the two sheets are pressed together. The horizontal and vertical pathways that when pushed together, let the controller register the precise location of the touch from any object, e.g. finger, stylus, pen, hand, by forming a contact.

In an alternative embodiment of this example the pathways in the x and y directions are formed as two layers in a single film. During operation of a four-wire touchscreen, a uniform, unidirectional voltage gradient is applied to the first layer, using the two wires to electrodes at each end of the sheet. The horizontal and vertical lines that are in the deformed area will be broken because the carbon particles in the conductive pathways will separated. When the sheet is pressed, the controller measures the voltage as distance along the first sheet, providing the X coordinate. When this coordinate has been acquired, the uniform voltage gradient is applied to the second layer using the two other wires to ascertain the Y coordinate. These operations occur within a few milliseconds, registering the touch location as contact is made.

Such a touchscreens typically have high resolution (4096×4096 DPI or higher), providing accurate touch control.

Due to the low particle loading the touchscreens will be more transparent, as the pathways will be practically invisible.

Example 5

A capacitive touchscreen is created from one layer of film with conductive pathways aligned in any direction. The pathways forms a capacitor that holds charge, e.g. from a voltage applied to the edges of the layer creating a controlled capacitor. When contact is made to the surface of the touchscreen, or a finger of a dielectric or conductive body is close to the touchscreen, the electric field across the touchscreen is changed The capacitive controller connected to the screen calculates the X and Y coordinates from the change in the capacitance as measured from the four corners of the film.

In another embodiment two or more layers are used, with eight or more wires to the corners of the film, four and four connecting to each layer, thus creating higher resolution when the controller switches between reading the layers, or if multiple controllers are used.

Example 6

Figure 5:
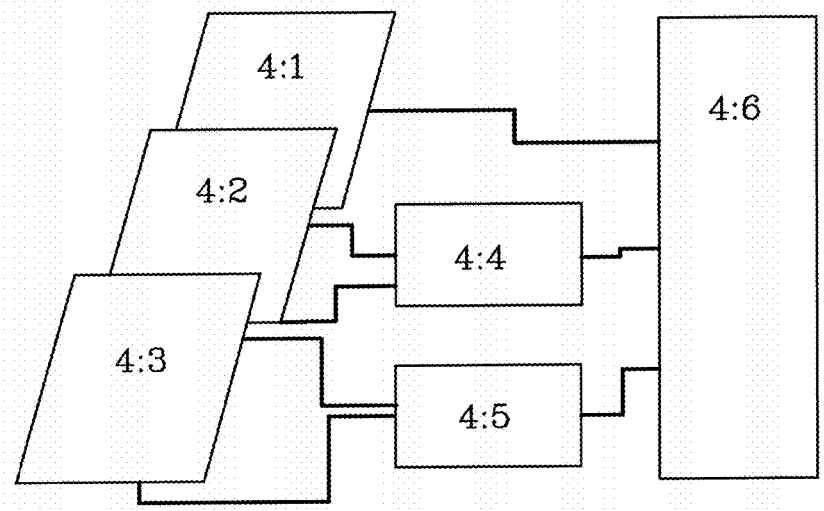

A hybrid screen is manufactured with resistive and capacitive layers as showed in FIG. 5. There could be more than one resistive and capacitive layer. In this embodiment both the position of proximity to and pressure on the sensor from e.g. a finger or stylus will be detected by the controllers and sent to the processor of the PC, mobile phone or similar device. In FIG. 5, the reference numbers indicates the following:

4:1—Display
4:2—Transparent capacitive sensor
4:3—Transparent resistive sensor
4:4—Capacitive controller
4:5—Resistive controller
4:6—Processor Example 7

Touch sensors to be used as in examples 5, 6 and 7 are formed using glass instead of a polymer as matrix.

Example 8

Figure 6A:
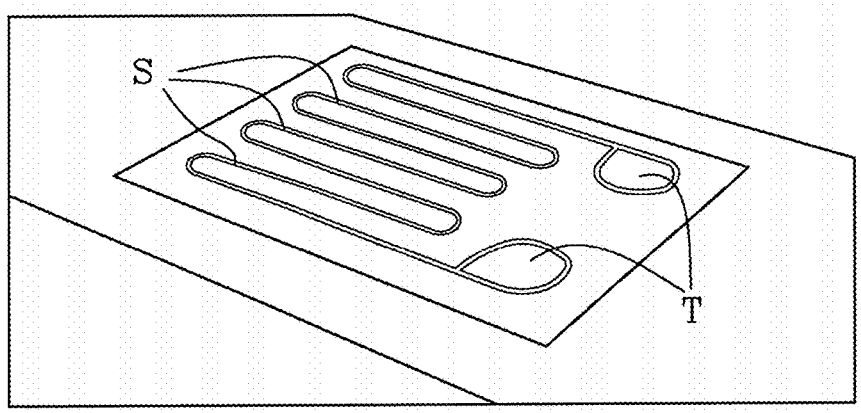
FIG. 6A shows schematics of a strain gauge having a strain sensitive pattern (S) between two terminals (T).
Figure 6B:
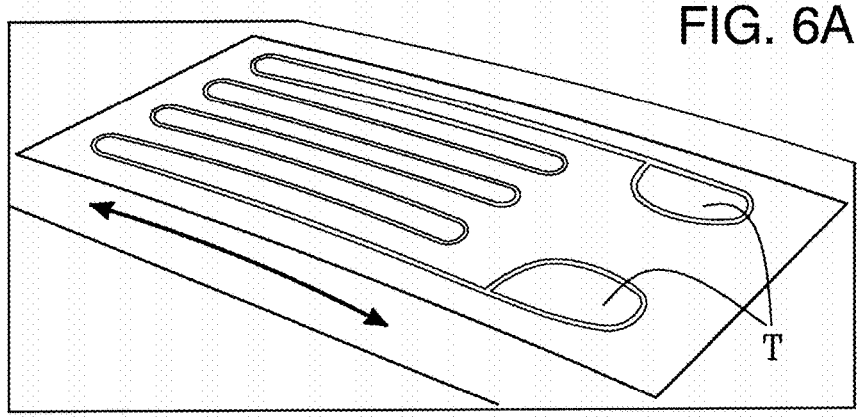
FIG. 6B shows schematics of a strain gauge when the matrix is tensioned.
Figure 6C:
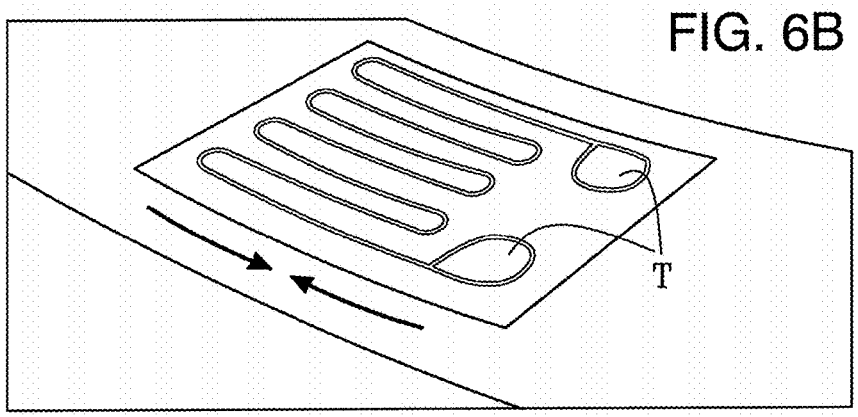
FIG. 6C shows schematics of a strain gauge when the matrix is compressed.

A strain gauge is formed by using a matrix that is an elastic polymer. As shown in FIG. 6A-6C the conductive pathways have been formed to a pattern suitable for a strain gauge by moving the field relative to the matrix. In a simpler embodiment the pattern is a straight line, or any other suitable pattern.

In FIG. 6A, the pathways form a strain sensitive pattern (S) between two terminals (T). When the matrix is tensioned (FIG. 6B), the area of the pathways narrows and the resistance increases, resulting in higher resistance between the terminals (T). When the matrix is compressed (FIG. 6C), the area thickens and the resistance decreases, resulting in a lower resistance between terminals (T).

Example 9

An electronic hygrometer, a humidity sensor is manufactured using capacitive sensors similar to that in example 5, but where the change in capacity is due to a change in the amount of water present in the matrix. In another embodiment the change in conductivity is measured. In one embodiment the matrix is made from cellulose. Temperature must also be measured, as it affects the calibration of these humidity sensors.

In one embodiment the alignment is in the z-plane, perpendicular to the substrate, and thus forming a structure similar to a carbon nanotube array. The alignment can also be in the x, y plane. The absorption and desorption of chemical vapours by the polymer matrix cause changes in the inter-tube distance or the electrical properties of the matrix and the conductance or capacitance changes.

Example 10

Figure 7:
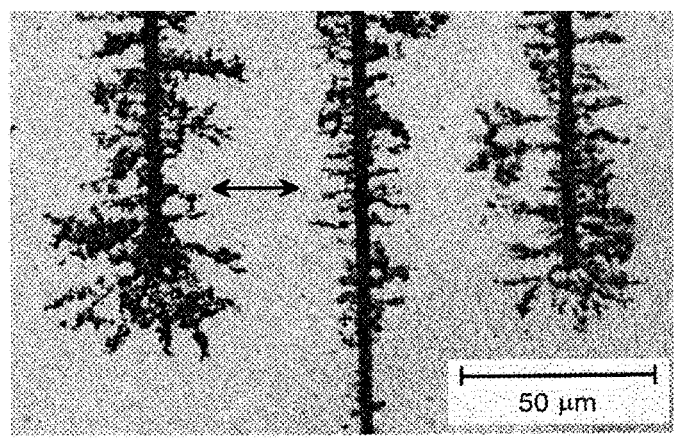
FIG. 7 shows dendritic pathways useful for capacitive sensing.

In order to produce a matrix with increased capacitance a procedure similar to that in example 1 was used, but the alignment was terminated before the chains reached from electrode to electrode. FIG. 7 shows so obtained electrodes with dendritic surface. This creates pathways that can hold more charge than the conductive pathways else produced.

The capacitance of this structure will be sensitive to deformation along the direction indicated by an arrow in FIG. 7.

Example 11

The example with the procedures similar to any of the claim 1, 2, 3, 4, or 5 but instead of other previously employed particles, spiky particles used in the QTCs are used.

Example 12

In this example aligned particles are used in a nanomechanical cantilever. This means that the cantilever is highly miniaturized and that instead of bulk layer the properties of single particles dominate.

Example 13

In this example a flexible sensor shaped as a thin sheet, coating or film is formed. It could be formed as part of the structure or as a material that is added on the whole or a part of the inner or outer surface of a body of a ship's hull, an aircraft or another vehicle or part there of (such as a car's engine), industrial machinery or on buildings, such as bridges or houses. It could also be used for packaging or as part of clothing, furniture or electronic equipment such as computers.

Example 14

This example is similar to example 13 but in addition the sensor function as at least one of an anti-static coating, a thermal conductor, an antenna and a shielding for electromagnetic waves due to the properties of the aligned pathways and the matrix that makes up the sensor.

Example 15

A micro-mechanical strain sensor made of carbon black (CB) particles assembled into a single wire in a polymer matrix was produced.

Figure 8A:
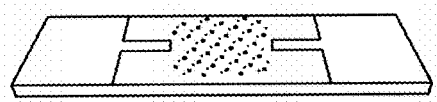
FIG. 8A illustrates schematically an experimental procedure for forming a strain sensor, where a low particle fraction mixture was spread between the electrodes.

The experimental procedure is shown in FIG. 8A-8D. CB particles (Alfa Aesar) were dispersed in UV-curable urethane methacrylate-based thermoset polymer Dymax 3094 (Dymax Corporation, CT). The particle fraction was 0.1 vol. %. This dispersion was spread to form a <10 µm layer on top of tiplike gold electrodes (FIG. 8A).

These electrodes were prepared using UV-lithography on a 250 µm thick silicon substrate covered by a insulating silicon oxide layer. Their thickness, width and mutual spacing were 100 nm, 3 µm and 100 µm, respectively. In the next step an alternating electric field of amplitude 3 kV/cm with a frequency of 1 kHz was applied over the sample using a custom-made voltage source. This led to the assembly of a particle string in between the electrode tips, FIG. 8B, in less than two minutes. The material was subsequently UV-cured by a mercury lamp. The resistance over the electrodes was monitored using a Keithley 2000 multimeter.

Figure 8B:
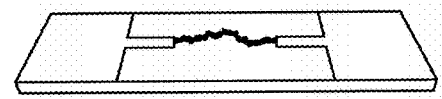
FIG. 8B illustrates schematically an experimental procedure for forming a strain sensor, where the low particle fraction mixture was aligned by an E-field between the electrode tips.
Figure 8C:
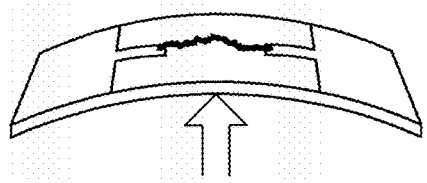
FIG. 8C illustrates schematically an experimental procedure for forming a strain sensor, where substrate was bent and the resistance of the strings was measured as a function of deflection.
Figure 8D:
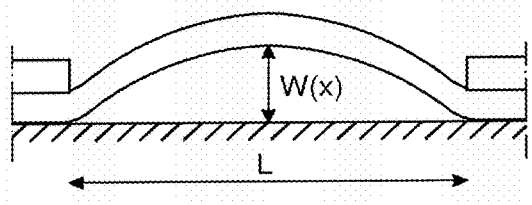
FIG. 8D illustrates schematically an experimental procedure for forming a strain sensor, where W(x) is the vertical deflection and L is the length of beam clamped at both ends.

FIGS. 8A-8D illustrate the experimental procedure. In FIG. 8A, a low particle fraction mixture was spread between the electrodes and aligned by an E-field into single strings by alternating electric field between the electrode tips in FIG. 8B. In FIG. 8C it is illustrated how this substrate was bent and the resistance of the strings was measured as a function of deflection. In FIG. 8D, W(x) is the vertical deflection and L is the length of the beam clamped at both ends.

The electromechanical properties of so prepared strings were studied by clamping the substrates under two clamps and bending them, as seen in FIGS. 8C and 8D.

The substrates were bent at the substrate centre, which leads to the stretching of the string on the surface. The resistivity of the string was measured as a function of the vertical deflection W(x) FIG. 8D. The surface strain and the resistivity increase with increasing bending. The strain on the surface corresponds to the strain in the string and the resistance through the string is increased with this strain.

Figure 9A:
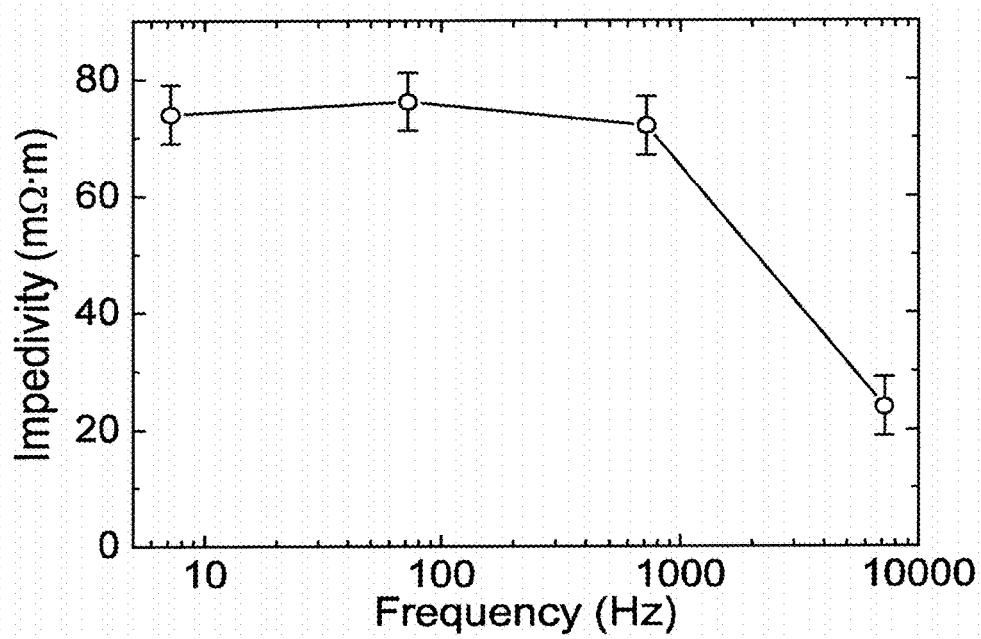
FIG. 9A shows the impedivity of an aligned CB string in cured polymer.
Figure 9B:
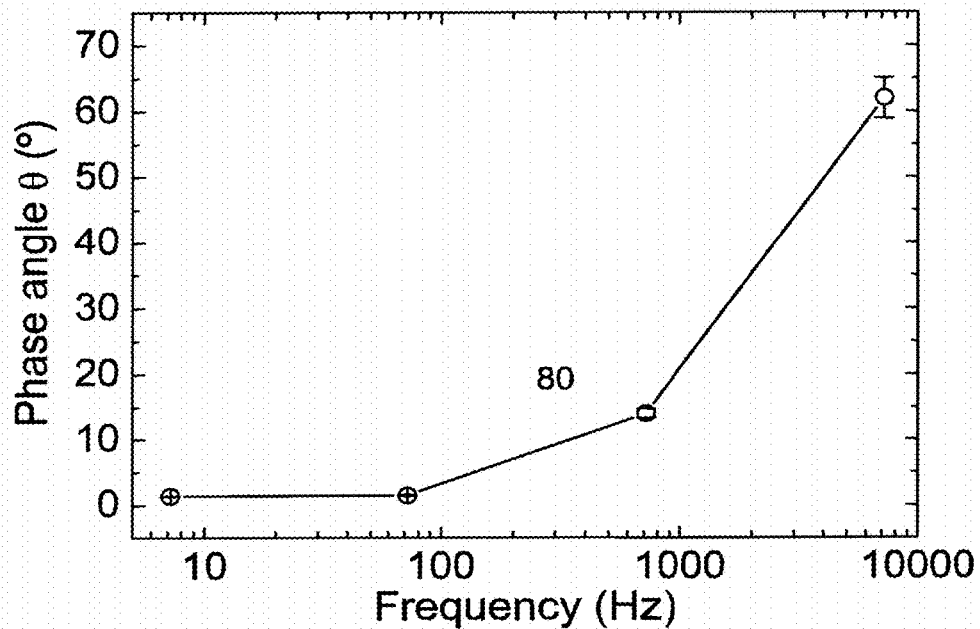
FIGS. 9B shows the phase angle of an aligned CB string in cured polymer.

FIG. 9A and FIG. 9B show the impedivity and phase angle θ, respectively as function of frequency of the aligned and cured CB particle string. The impedivity is nearly constant up to 1 kHz and decreases for higher frequencies. The phase angle begins to deviate from zero at 100 Hz, indicating a contribution from the capacitive conductivity.

FIG. 9A illustrates impedivity and FIG. 9B illustrates phase angle of an aligned CB string in cured polymer.

Figure 10A:
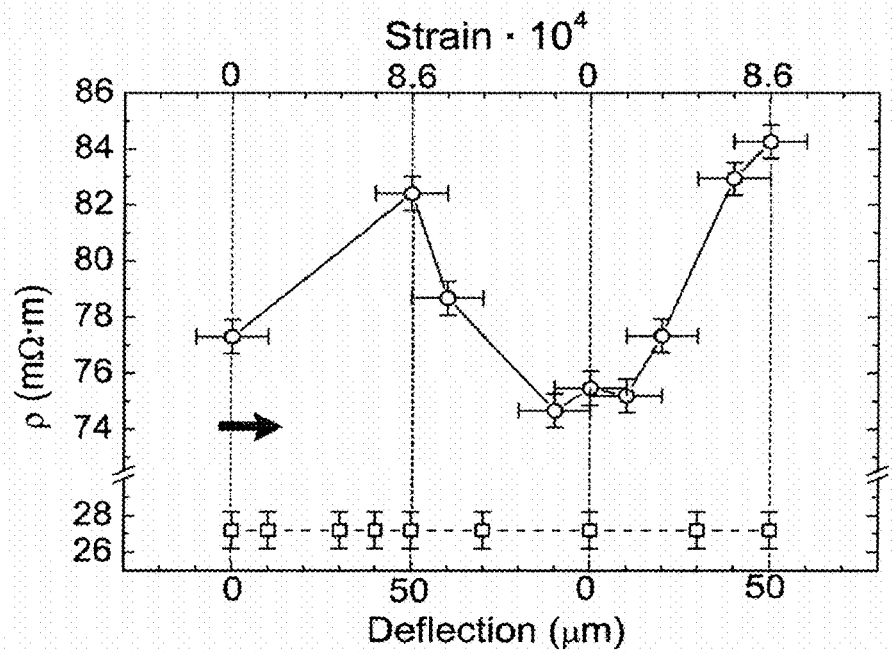
FIG. 10A illustrates the resistivity of an aligned string of CB particles as a function of deflection.

FIG. 10A shows the resistivity of the single string in a cured polymer matrix as a function of deflection. Also shown are corresponding data for the nonaligned film containing 12 vol. % of CB particles, i.e., a fraction well above the percolation threshold. The strain corresponding to a given deflection is also presented in the graph and is the relative displacement of particles in the polymer with deformation. The vertical dotted lines mark the change of deflection direction. The samples were bent from a relaxed state at 0 µm to a deflected state at 50 µm, then back to the relaxed state, and lastly bent to 50 µm once more. These measurements were done subsequently with the same samples. For the aligned sample, the data show an increase in resistivity with 50 µm deflection. The original resistivity is restored on the release and the increase is again seen with next deflection.

Figure 10B:
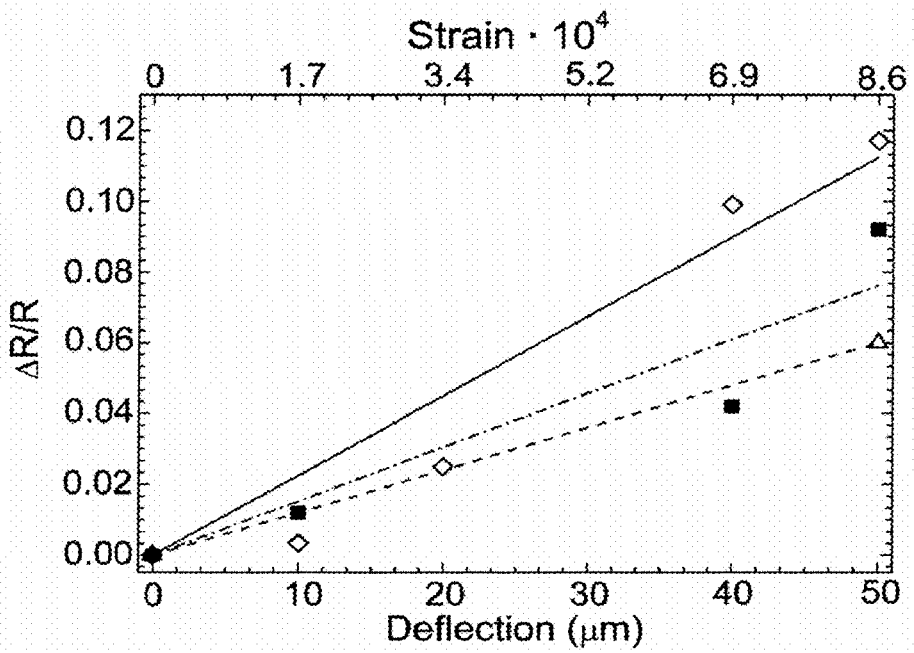
FIG. 10B illustrates the relative change in resistance for the aligned string as a function of deflection.

FIG. 10A illustrates the resistivity p of an aligned string of CB particles (circles) with the initial 0.1 vol. % particle loading, and a non-aligned sample with the 12 vol. % particle loading, (squares) as function of deflection D. The dotted lines mark the change of deflection direction. FIG. 10B illustrates the relative change in resistance for the aligned string as a function of deflection. The open triangles and diamonds show the first and third deflection, respectively. The solid squares show the first release. Dashed, solid and dash dotted lines are corresponding linear fits.

FIG. 10B shows the relative change in resistance for the first and second deflection plus the first release of the aligned sample corresponding to FIG. 10A. A gauge factor estimated for the aligned string is about 150 with an error margin of 10%, as estimated from these slopes using Eq. 1 ($\Delta R/R = K \cdot S$, where K is the gauge factor and S is the strain). This is significantly higher than that of a nonaligned, high-particle fraction sample, which did not show any measurable effect due to the stretching. This means that the alignment has significant benefits in both the conductivity enhancement and in the strain sensitivity.

Results reported earlier (by Gammelgaard et al.) show that a SU8 polymer mixed with high concentration (16%) of isotropic CBs have a gauge factor of 15-20. Thus a gauge factor about 10 times higher may be obtained with an aligned single string compared to an isotopic high particle fraction sample.

In conclusion, single strings of CB particles were aligned by dielectrophoresis in UV-curable Dymax 3094 polymer matrix and shown to be a promising candidate as a strain sensor. By deforming these single strings in-plane, a reversible change in resistivity was observed, similar to what has been reported before 8 for non-aligned CB-SU8 polymer composite when the particle fraction exceeds the percolation threshold. A gauge factor of 150 was found, exceeding the value of 15-20 reported previously. Detection of significant gauge factors for nonaligned CB-Dymax 3094 composites with the particle fraction exceeding the threshold was not possible.

Higher gauge factors could be achieved by using different particle sizes, particles size distributions or by improving the conductivity of the nanoparticles.

Example 16

In another embodiment, carbon black particles were aligned in an elastomeric matrix. The particles were carbon black particles 0.0004 g, and the elastomer Dow Corning 734 Flowable Sealant (silicone based elastomer), 0.6700 g. A solvent, 2-Butanone, 0.5941 g were used to decrease the viscosity of the elastomer. The particle concentration was 0.03 wt %.

The resulting elastomeric matrix including aligned CB particles displayed behaviour where the resistance of the conductive path of CB particles decreased with compression of the elastomer.

Figure 11:
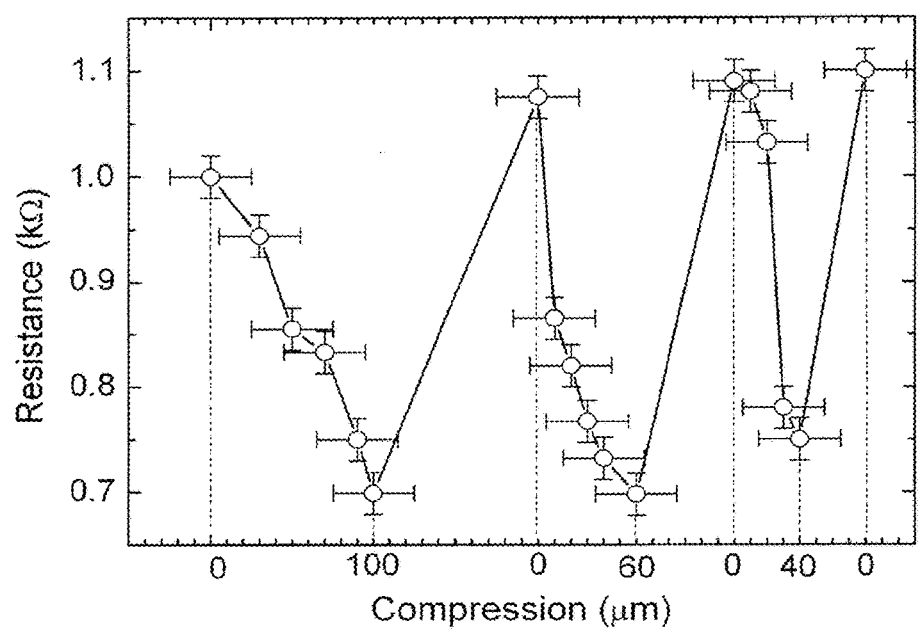
FIG. 11 illustrates the relationship between resistance and compression of a sensor in accordance with another embodiment of the invention.

FIG. 11 illustrates the resistance through the conductive path versus compression of out-of-plane aligned CB articles in the matrix of Dow Corning 734. This means that the sample is sheetlike and the aligned strings are formed parallel to its surface normal, thus connecting two largest surfaces through the sheet. The electrode had an initial spacing of about 150 µm. The data correspond to three subsequent compressions. It is seen how the resistance decreases with each compression and resumes a higher value when the compression is released. An alternating electric field of 1.5 kV/cm for 5 min. The sample was humidity-cured for 24 hours. The resistances were measured with Keithley 2000 millimeter.

Example 17

Alignment of single strings of CNCs in Dymax 3094 polymer was performed. CNCs were mixed with urethane methacrylate based Dymax 3094 with a particle fraction of 0.1 vol. %. This particle fraction is an order of magnitude lower than expected percolation threshold (~2 vol. %). The low particle fraction suppresses aggregation thereby rendering a uniform mixture with the particle size below 3 Since the size of CNC particles are between 100 nm and 3 the CNCs are believed to be nearly perfectly dispersed. The alignment was done by spreading a thin (1-10 µm) layer of this dispersion over the tip-like electrodes and applying an alternating electric field between the electrodes followed by UV-curing, as seen in FIG. 8A-8C (details can be found in the Experimental section below).

Figure 12:
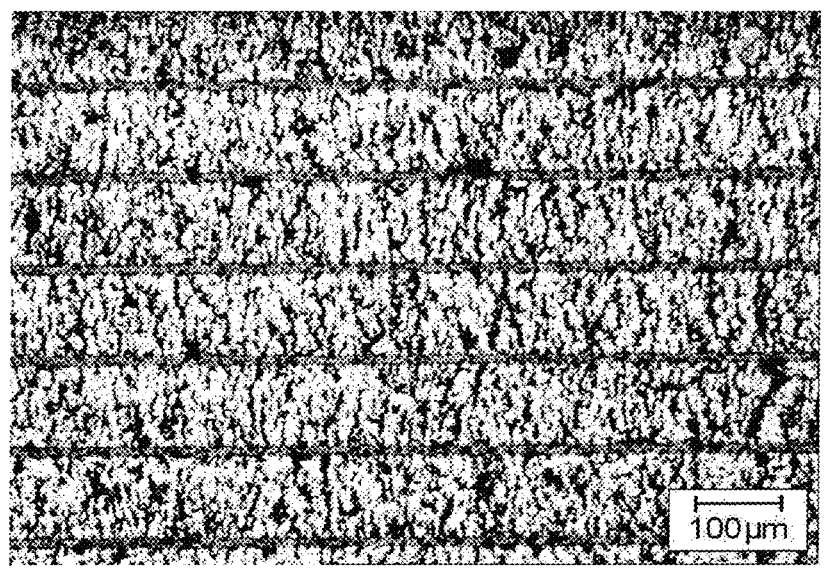
FIG. 12 is an image of multiple aligned strings of CNCs in an embodiment of the invention.

FIG. 12 Multiple aligned strings of CNCs in a cured Dymax 3094 polymer on interdigitated electrodes.

FIG. 13A to 13D show micrographs of the assembly of a string of CNCs over time. The applied field is E=4 kV/cm over an electrode spacing of 100 µm. Originally isotropic mixture had the particle fraction of about 0.1 vol. %. FIG. 13A illustrates particles dispersed in the polymer before the electric field was applied. Snapshots of the alignment process after 45 seconds FIG. 13B and 1 minute 20 seconds FIG. 13C. A complete string was formed within 2 minutes 20 seconds FIG. 13D.

Hence, a conducting string between two electrodes with a spacing of 100 µm was produced in less than 150 seconds.

Prior to the alignment, the resistance of the mixture is in the MΩ range. The alignment causes the resistance to drop over three orders of magnitude to the kΩ range. For instance, the aligned string shown in FIG. 13D had a resistivity of p=40 mΩ·m. UV-curing of the polymer composite will locks the aligned carbon particles, making electrical characterization of the aligned strings possible. The alignment and conductivity are maintained upon curing.

FIG. 14 shows a close-up of an aligned string after curing with a resistivity of $\rho=32$ mΩ·m. This is an UV-cured single string of aligned CNC particles spanning an electrode gap of 100 μm.

EXPERIMENTAL

Materials and Sample Preparation

The samples contained carbon particles dispersed in a polymer matrix. The employed CNC material was supplied by n-TEC AS (Norway) and it contained about 70% discs, 20% nanocones and 10% carbon black. The material had been heat treated to 2700° C. prior use. The employed CB was supplied by Alfa Aesar. The polymer used was Dymax 3094 Ultra Light-Weld (Dymax Corporation, CT) supplied by Lindberg & Lund AS (Norway). This is an urethane methacrylate based UV-curable thermoset polymer. Carbon particles were dispersed in the polymer by stirring at 150 rpm for 15 minutes, which leads to a uniform dispersion with the particle size less than 10 μm.

The alignment procedure is shown in FIGS. 8A-8C. The gold electrodes were made by UV-lithography on a 250 μm thick silicon wafer covered by a 300 nm thick insulating silicon oxide layer, and consisted of two 100 nm thick and 3 μm wide fingers facing each other with the spacing d ranging from 10 to 100 μm.

A layer (<10 μm) of dispersion was smeared on top of the electrodes (FIG. 8A). An electric field of ~4 kV/cm with a frequency of 1 kHz was applied over the electrodes (FIG. 8B). The dielectrophoresis effect causes the particles to move towards the two electrode tips, forming continuous strings at the edge of the tips. The strings would grow from each electrode tip until they met at the halfway point of the electrode gap forming a continuous conducting string (FIG. 8C). The alignment occurs within 1-3 minutes, depending on particle concentration and the applied electric field. The particles will stay in place after the electric field is turned off, but the characterization or moving of the sample may destroy the aligned string. The polymer is therefore subsequently UV-cured by a mercury lamp for 5 minutes, locking the particles into place.

For the DC conductivity measurements, 20 similarly prepared parallel samples of CNCs and CB particles were aligned in Dymax 3094. The resistance was monitored by a Keithley 2000 multimeter over the alignment electrodes immediately after alignment without UV-curing.

Electrical and Electromechanical Characterization

The electromechanical experiment is illustrated in FIG. 8D. The samples were clamped at both ends and a micrometer screw was used to control a small blade at the center of the substrate. The blade would begin to bend sample thus stretching the carbon string on its upper surface. The samples were deflect by a given deflection and the relaxed, and then bent yet again several times in a continuous manner. An IV curve was measured for every deflection point and used for determining the resistance for each point. The resistance through the sample increases with increasing bending.

Electrical Properties of Aligned Strings

Figure 15:
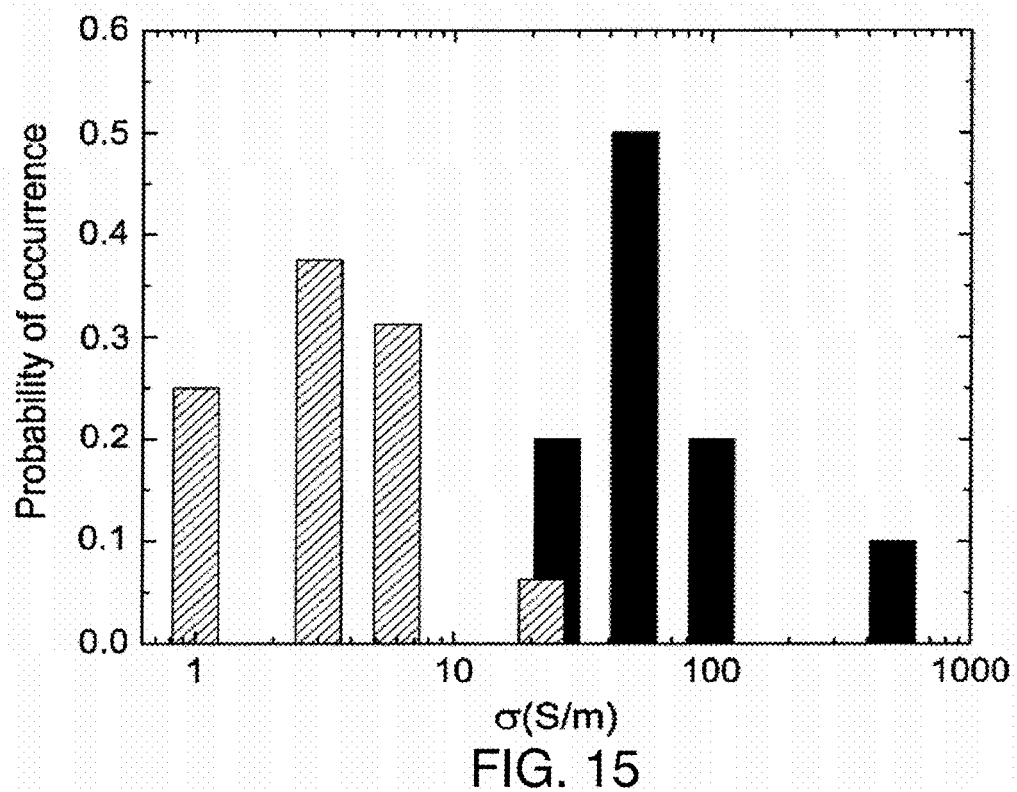
FIG. 15 is a comparative figure schematically showing sample fraction versus conductivity for aligned CB and aligned CNC.

The DC conductivity of 20 identically aligned samples prepared in accordance with the above were measured for both CNCs and CB particles. The distributions of these conductivities are shown in FIG. 15. FIG. 15 illustrates the sample fraction versus conductivity for aligned CB (striped) and CNC (black) in Dymax 3094 polymer. The CNCs have higher conductivity but have a smaller probability to produce a conducting string. Only fifty percent of the aligned single strings of CNC were conducting and the nonconducting strings are not included in the shown probability distribution.

The figure is normalized so that the probability of producing a conductive string is unity in both cases. The CNC strings have a higher conductivity than the CB strings.

The CNC particle strings have conductivities ranging from 25 to 500 S/m, with 90% falling in the region below 100 S/m. The CB particles have conductivities ranging from 1 to 22 S/m, with 95% falling in the region below 6 S/m. Though the conductive CNC particle strings have a higher conductivity, only 10 out of 20 prepared samples conducted any measureable current. These nonconductive strings are not included in FIG. 15. However, all 20 the CNC particle strings appeared visually complete and were therefore expected to be conductive. This implies that tiny, optically invisible mismatches between particles are enough to prevent a conductive pathway. One reason for this difference between CNCs and CB may stem from the different particle topology. Another reason may be the polydisperse nature of the CNC particles. The cones and discs might have difficulties creating good "topologically matching" connection between each other due to the variable shape of the particles.

The conductivity of an intact string provides an estimation for the uppermost conductivity of the earlier reported multi-string samples like the one shown in FIG. 12. As the former is significantly higher (for CNCs 25-500 S/m, see FIG. 15) than the conductivity of multi-string samples normalized to the volume fraction of particles (0.1-1 S/m), this indicates that a large part of seemingly intact strings in the multi-string samples (FIG. 12) are actually broken. The conductivity gap between single strings and multi-string samples could potentially be reduced by optimizing the preparation of larger samples for example using even and vibration free preparation setups.

Figure 16:
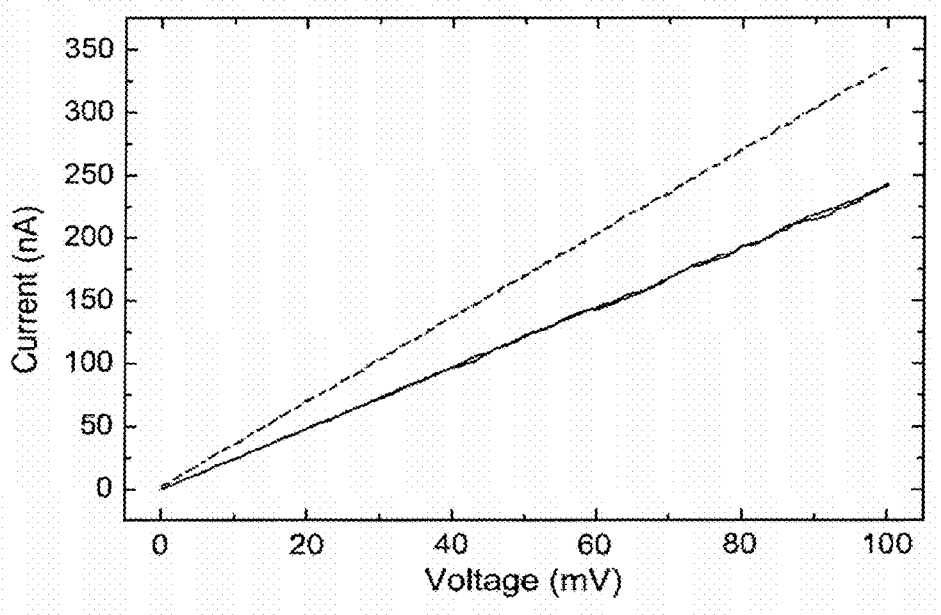
FIG. 16 is a comparative figure showing current to voltage or an aligned sample and a non-aligned sample.

FIG. 16 plots the current-voltage curves of an aligned low particle fraction sample and a nonaligned high particle fraction sample. The solid line is from an aligned sample prepared from the isotropic CNC-polymer mixture with a concentration of 0.1 vol. %, while the dashed line represents the nonaligned sample with a concentration of 13 vol. %. The direct current through both samples grow linearly with increasing voltage up to 100 mV and no sign of hysteresis is observed on cycling. The nonaligned sample has a marginally higher conductivity than the aligned one but they are both of the same order of magnitude.

Figure 17:
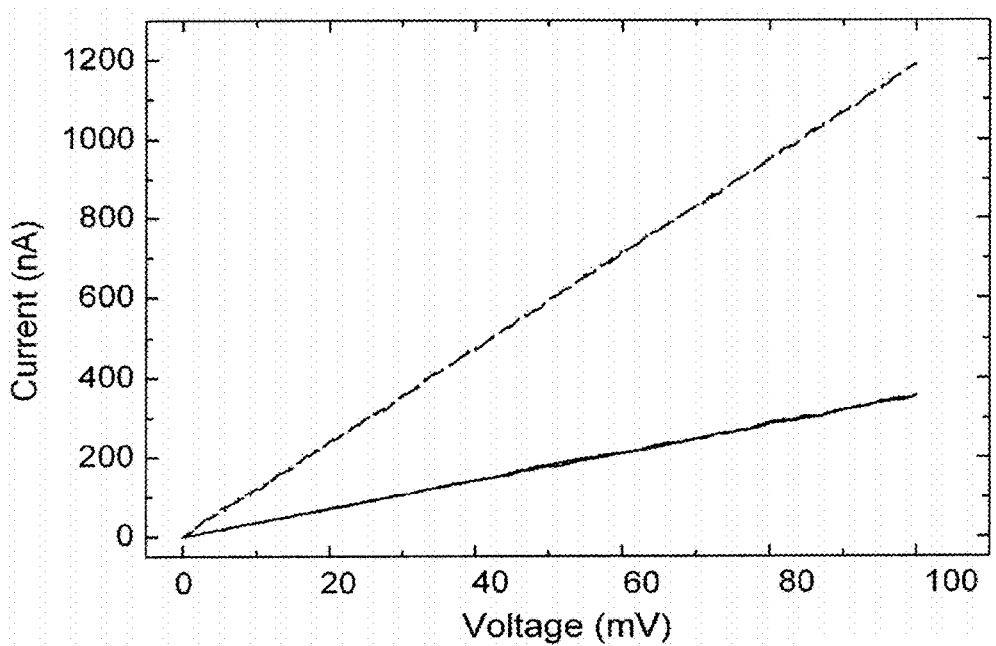
FIG. 17 shows the direct current through the sample grows linearly with increasing voltage up to 100 mV and no sign of hysteresis is observed on cycling.

FIG. 17 The direct current through the sample grows linearly with increasing voltage up to 100 mV and no sign of hysteresis is observed on cycling.

Figure 18A:
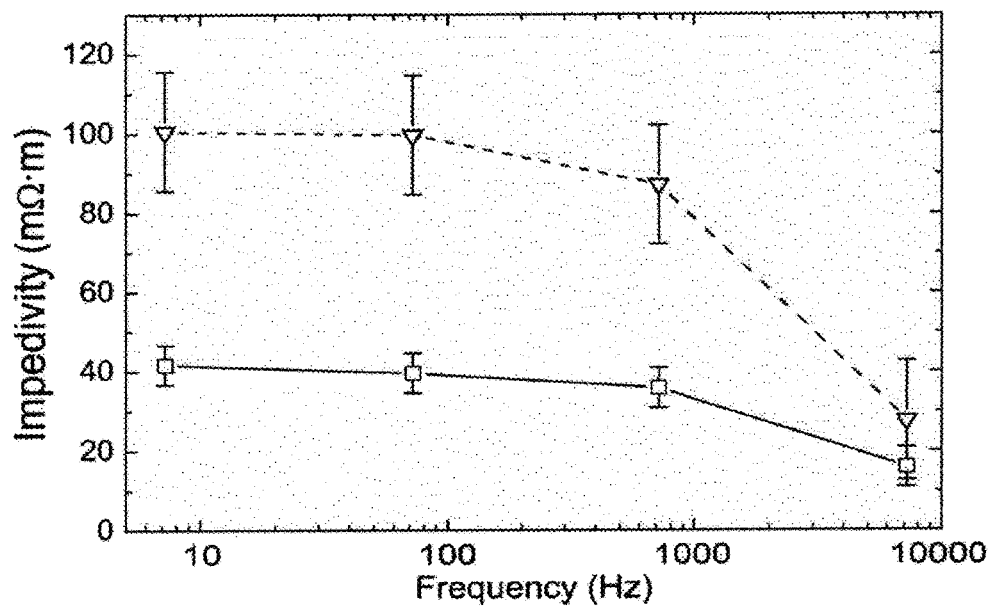
FIG. 18A shows AC impedivity of aligned CNC film and isotropic CNC film.
Figure 18B:
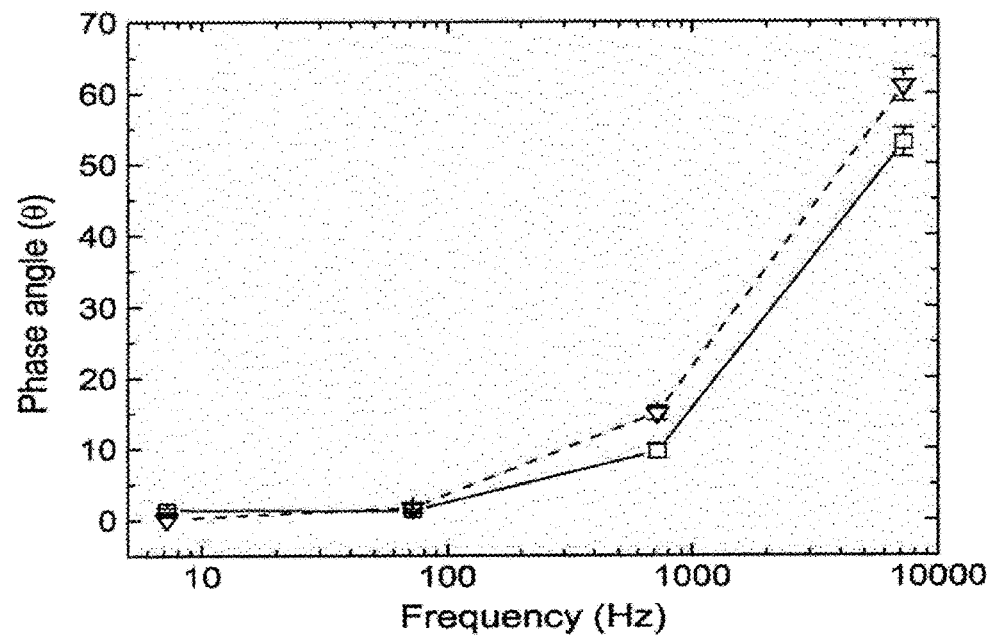
FIG. 18B shows the phase angle of aligned CNC film and isotropic CNC film.

FIGS. 18A and 18B plot the impedivity and phase angle vs. frequency for both an aligned sample and a non-aligned, high particle-fraction sample. AC impedance data of aligned CNC strings (squares) and isotropic CNC film with high particle fraction (13 vol %) in Dymax 3094 polymer (triangles). FIG. 18A impeditivity as a function of frequency, FIG. 18B phase angle as a function of frequency.

Both samples behave very similarly when the frequency is increased. The impedivity is nearly constant up to 1 kHz, but falls noteworthy between 1 kHz and 10 kHz. The phase angle begins to deviate from zero at 100 Hz, indicating the rise of capacitive conductivity. The similarity between aligned and nonaligned samples implies that the aligned string behaves essentially as bulk, heavily loaded CNC composite. These data are also consistent with the AC-impedance of multi-string samples indicating the Ohmic nature of the strings. However, the data differs from the data of nonaligned CNC polymer mixtures at low particle fraction where the phase angle begins to differ from zero much earlier (>10 Hz), pointing to the ionic conductivity of the polymer.

Electromechanical Properties of Aligned Strings

Next, electromechanical measurements of the CNC strings in cured matrix were performed. The samples were clamped at both ends and deflected gradually in the centre as shown in FIG. 8D. The deflection leads to the stretching of the surface layer and thereby causes an increasing strain of the aligned film and presumably moves the particles with respect to each other. The measurements were conducted by deflecting the samples several times and measuring the resistivity for every deflection point.

Figure 19A:
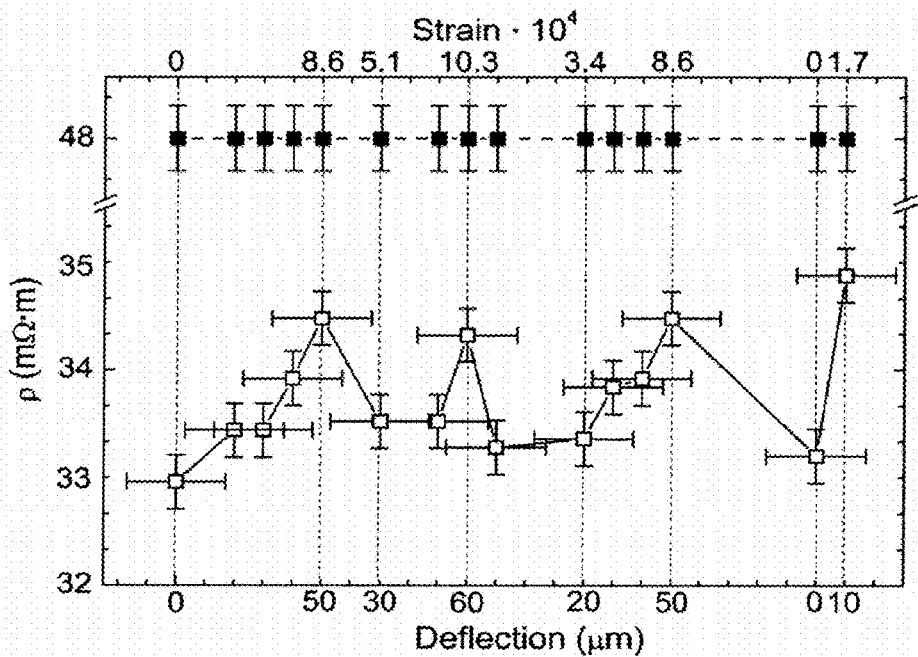
FIG. 19A illustrates resistivity as a function of deflection for an aligned CNC string versus a nonaligned sample.
Figure 19B:
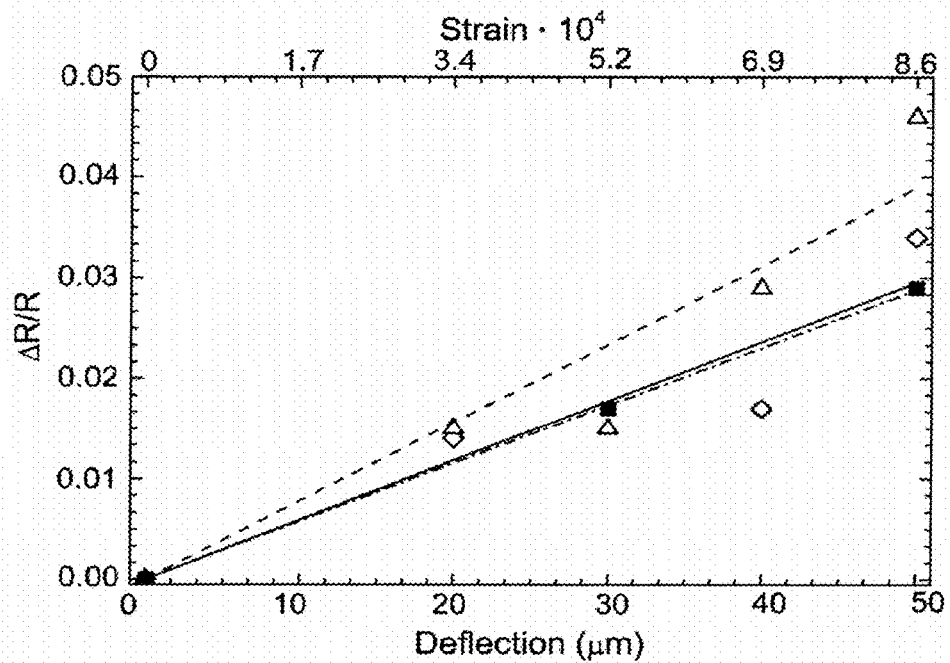
FIG. 19B illustrates the relative change in resistance as a function of deflection for the aligned string.

FIG. 19A illustrates resistivity as a function of deflection for an aligned CNC string (open squares) and nonaligned sample with high 13 vol. % particle fraction (solid square). The dotted lines mark the change in deflection direction. FIG. 19B The relative change in resistance as a function of deflection for the aligned string. The open triangles show the first deflection while the open diamonds represent the third deflection. The solid squares show the first release. Dashed, dash dotted and solid lines are corresponding linear fits.

FIG. 19A shows the so obtained resistivities for an aligned sample as a function of deflection. The corresponding data of nonaligned sample is shown for comparison. The aligned sample was prepared from the dispersion with a particle fraction of 0.1 vol. % and is the exact same sample as shown in FIG. 14. The nonaligned sample had a particle concentration of 13 vol. %. The resistivity at each deflection point was calculated by linear fits to separate IV curves measured at each point. This method is justified by the ohmic behaviour of strings for DC and low measurement frequencies. The top axis shows the induced strain of the strings defined as the relative displacement of particles due to an applied external force. The measurements were done in a continuous manner and the vertically dotted lines mark the change of deflection direction. When the deflection goes from 0 to 50 μm to 30 μm in FIG. 19A, it means that the sample was deflected from a relaxed state at 0 deflection to a deflected state at 50 μm and relaxed to a less deflected state at 30 μm. The deflection has a significant and reversible effect on the resistivity of the aligned sample, the resistivity increasing with the increasing deflection and strain. In contrast, the resistivity of nonaligned sample does not show any measureable effect.

FIG. 19B shows the relative change in resistance calculated from the first and second deflections as well as the first release of the aligned sample (FIG. 19A). These data gives a gauge factor of 50 with an error margin of 10%, as estimated from the slopes in FIG. 19B, using Eq. 1. This shows that the alignment has a significant effect making both conductive and piezoresistive CNC materials possible. The aligned string performs well against its standards of comparison. The obtained gauge factor is higher than those of typical thick-film resistors, whose gauge factors range from 3-30 and also compares well to that of an optimized silicon piezoresistive cantilever. The gauge factor is also notably higher than typical values reported for aligned multi-walled carbon nanotubes, for which values of about 1.5 and 3 have been reported for particle concentrations of 0.75 wt-% and 0.5 wt-%, respectively.

In this work, the strain was calculated at the top surface of the substrate, and it was assumed that the strain experienced by the composite layer with the particle string, was the same. This is only correct if the composite layer thickness is well below the substrate thickness, but this condition was fulfilled in our experiments.

It will be understood that a person skilled in the art may readily envisage numerous alternatives to the above-described example embodiments. In particular, the described features may be varied or combined to form new embodiments.

The invention claimed is:

1. A method for forming a sensor on a substrate, the method comprising, in the following order:
   a. forming a layer of a mixture comprising a matrix and conductive particles on a substrate, the mixture having a first viscosity which allows the conductive particles to rearrange within the layer;
   b. applying an electric field over the layer with electrodes, so that a number of the conductive particles are assembled and aligned with the electric field, thus creating one or more anisotropic conductive pathways in the layer, wherein at least one of the electrodes that applies the electric field to assemble and align the conductive particles is not in direct contact with the layer while the electric field is applied;
   c. changing the viscosity of the layer to a second viscosity, said second viscosity being higher than the first viscosity, in order to mechanically stabilize the layer and preserve the one or more anisotropic conductive pathways.

2. The method in accordance with claim 1, further comprising, after step c:
   d. totally or partly removing the matrix from the layer.

3. The method in accordance with claim 1, wherein the conductivity of the pathways is changed if the matrix is deformed.

4. The method in accordance with claim 1, wherein the conductive particles comprise at least one material selected from the group consisting of carbon, metal, metal oxides, ceramics, and piezoelectric material.

5. The method in accordance with claim 1, wherein the conductive particles are conductive from quantum tunneling effects.

6. The method in accordance with claim 1, wherein the number of conductive particles in step a) is below a percolation threshold.

7. The method in accordance with claim 1, wherein the electrodes that apply the electric field are a pair of alignment electrodes that are at fixed position relatively to a substrate on which the layer is applied.

8. The method in accordance with claim 7, wherein one of the alignment electrodes is in direct contact with the layer while the electric field is applied with the alignment electrodes.

9. The method in accordance with claim 7, wherein the alignment electrodes are insulated from the layer.

10. The method in accordance with claim 1, wherein the electric field applied over the layer with electrodes is either an AC or a DC-electric field on the order of 0.05-35 kV/cm.

11. The method in accordance with claim 1, wherein the conductive particles have an aspect ratio range of 1-20.

12. The method in accordance with claim 1, wherein the conductive particles comprise irregular graphitic particles, spherical carbon black (CB) particles, disc-like particles, or conical carbon particles (carbon nanocones CNCs).

13. The method in accordance with claim 1, wherein the matrix is a thermoset polymer, a thermoplastic polymer system, a lyotropic system or a mixture thereof.

14. The method in accordance with claim 1, wherein the matrix comprises a UV-curable polymer.

15. The method in accordance with claim 1, wherein the matrix comprises an elastomer.

16. The method in accordance with claim 1, wherein the electric field applied over the layer with electrodes is either an AC or a DC-electric field on the order of 0.1-10 kV/cm.

17. The method in accordance with claim 1, wherein the conductive particles have an aspect ratio of 1-10.

18. The method in accordance with claim 1, wherein the conductive particles have an aspect ratio of 1-5.

19. The method in accordance with claim 1, wherein the conductive particles have an aspect ratio of 1-4.

20. The method in accordance with claim 1, wherein the conductive particles comprise carbon.

21. The method in accordance with claim 1, wherein the conductive particles are irregular graphitic particles.

22. The method in accordance with claim 1, wherein the conductive particles are spherical carbon black (CB) particles.

23. The method in accordance with claim 1, wherein the conductive particles are conical carbon particles (carbon nanocones CNCs).

24. The method in accordance with claim 1, wherein the electrodes that apply the electric field are a pair of alignment electrodes that are moved relatively to a substrate on which the layer is applied.

25. The method in accordance with claim 24, wherein one of the alignment electrodes is in direct contact with the layer while the electric field is applied with the alignment electrodes.

26. The method in accordance with claim 24, wherein the alignment electrodes are insulated from the layer.

* * * * *